United States Patent [19]
Minkofski

[11] Patent Number: 6,091,825
[45] Date of Patent: Jul. 18, 2000

[54] SOUND BAFFLING DEVICE

[76] Inventor: Horst Burghardt Minkofski, 349 W Georgia St., Vancouver, BC, Canada, V6B 3P7

[21] Appl. No.: 08/613,685

[22] Filed: Mar. 11, 1996

[51] Int. Cl.[7] .................................................... A61F 11/06
[52] U.S. Cl. ................................................................ 381/72
[58] Field of Search ................................... 381/314, 372, 381/371, 370, 373, 72, 317, 318, 322, 374, 189, 312, 71.6, 71.7, 94.1

[56] References Cited

U.S. PATENT DOCUMENTS

| | | | |
|---|---|---|---|
| 4,658,931 | 4/1987 | Curry | 381/372 |
| 4,809,811 | 3/1989 | Gorkike | 381/372 |
| 4,989,271 | 2/1991 | Sapiejewski et al. | 381/372 |
| 5,148,887 | 9/1992 | Murphy | 381/372 |
| 5,182,774 | 1/1993 | Bourk | 381/372 |
| 5,208,868 | 5/1993 | Sapiejewski | 381/372 |
| 5,241,971 | 9/1993 | Lundin | 381/372 |

Primary Examiner—Vivian Chang

[57] ABSTRACT

A sound baffling device comprising an enclosure containing a homogeneous means for attenuating sound, the shape and composition of said enclosure crafted to vary the sound baffling characteristics of said enclosure, and another embodiment showing how a workable material comprised of a plurality of enclosures containing a homogeneous means for attenuating sound may be used to baffle sound. A method for constructing the workable material is given and various applications to sound baffling requirements involving previous as well as new uses are set out, including a description of how dynamic sound baffling may be implemented.

More specifically, the invention shows improvements to the sound baffling cups of ear protectors and the application of sound baffling cups to head phone sets, including some of the new art required to render these applications more effective. Several fitting means are described and improvements to the connecting means of head phone sets are discussed. The combination of previously known sound baffling cups with head phone sets is also set out.

24 Claims, 19 Drawing Sheets

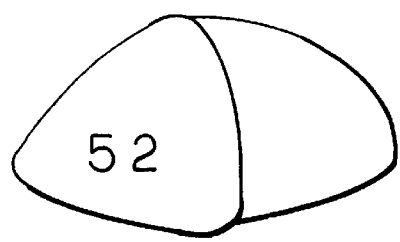
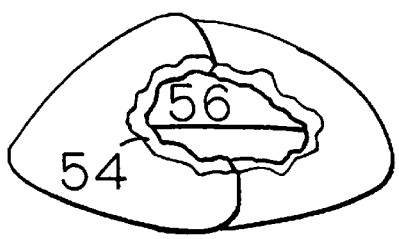
FIG. 1    FIG. 2
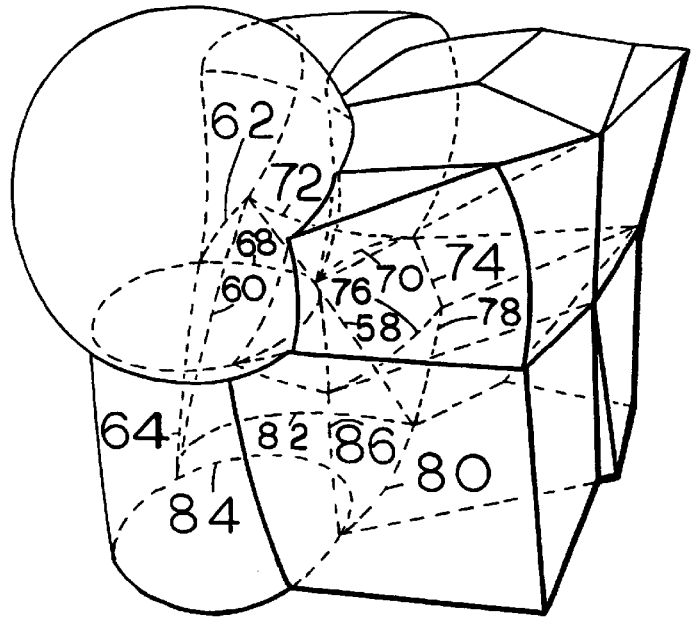
FIG. 3
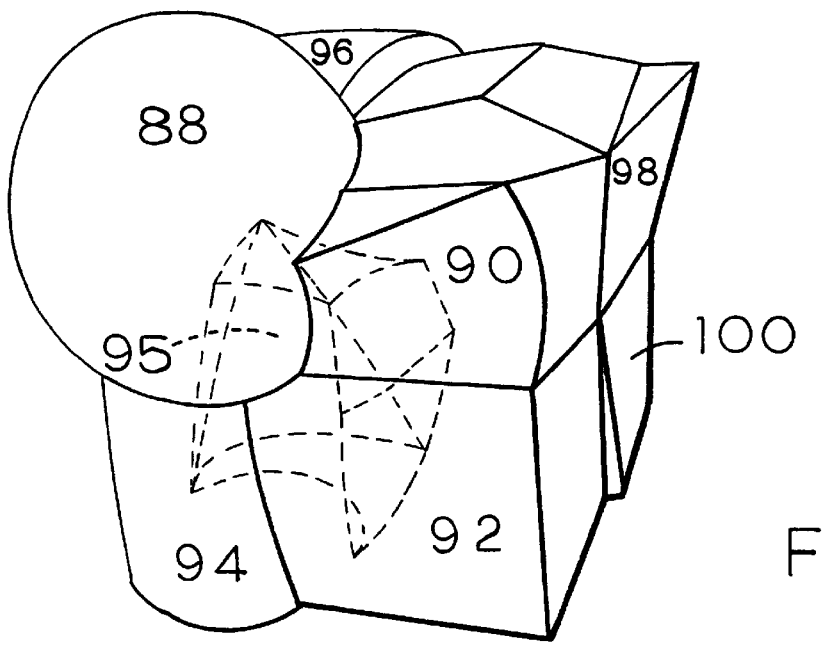
FIG. 4

FIG. 7B
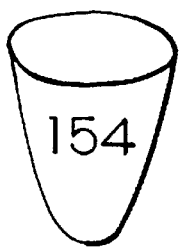
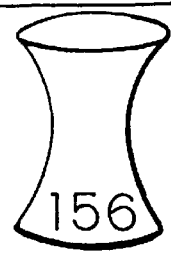
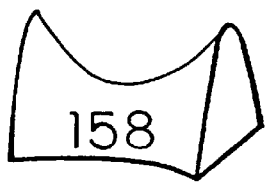
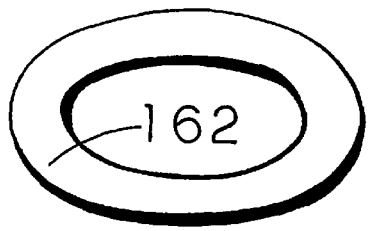
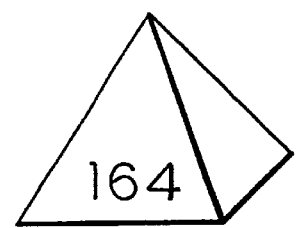
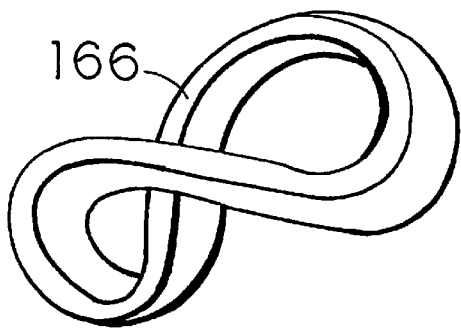
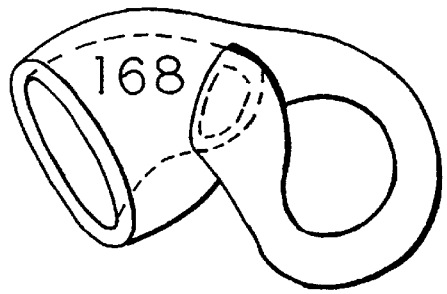

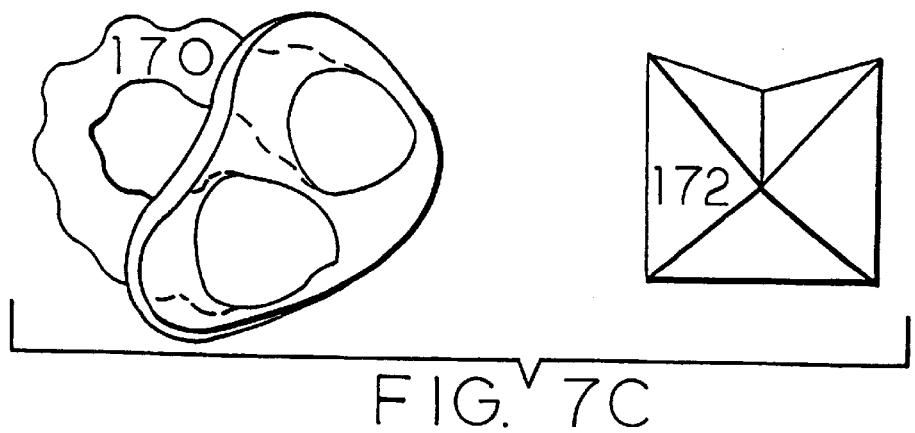
FIG. 7C
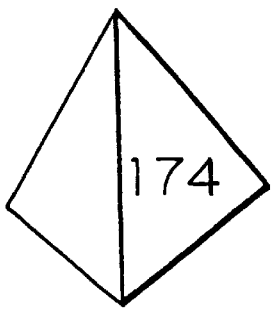
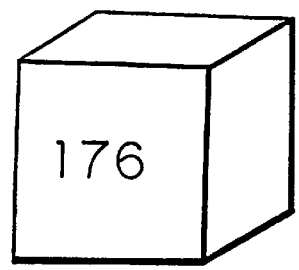
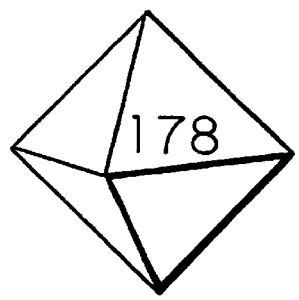
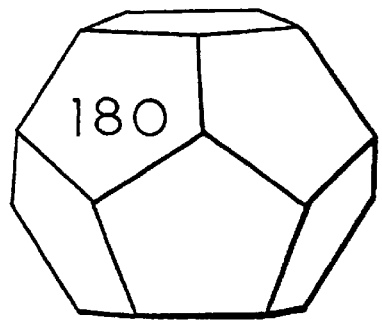
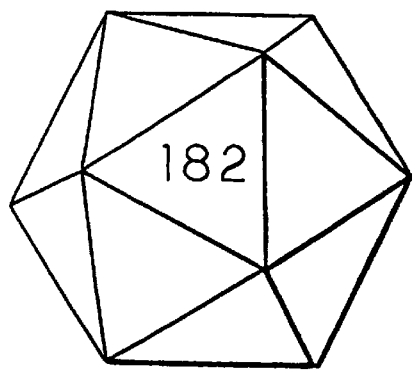
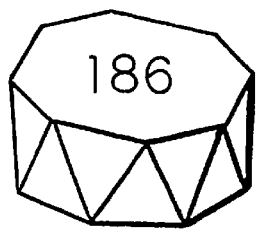
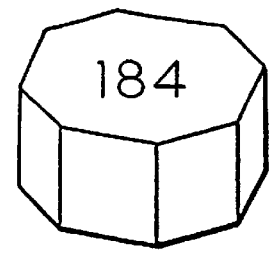
FIG. 8

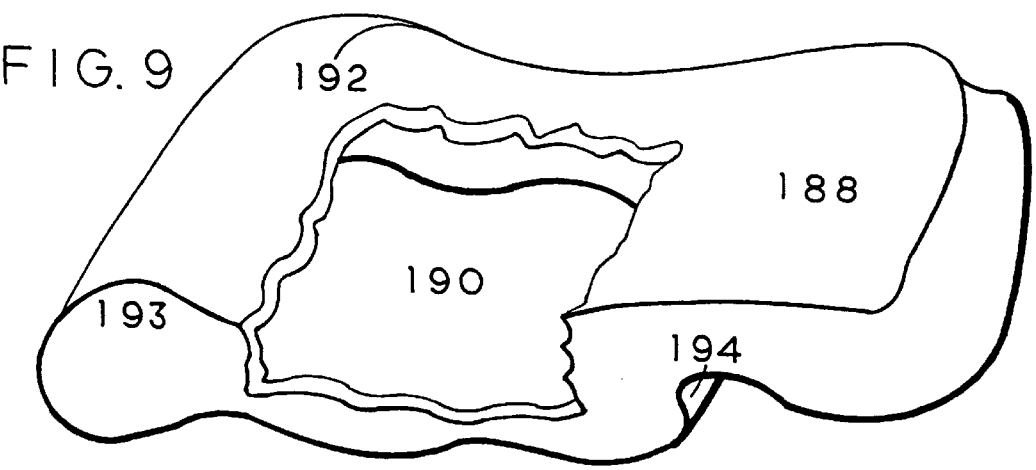
FIG. 9
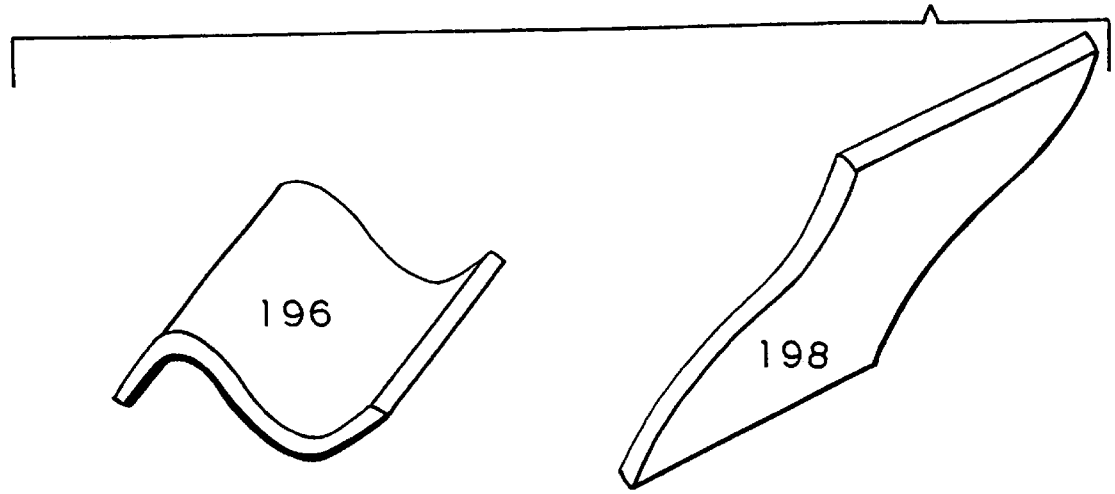
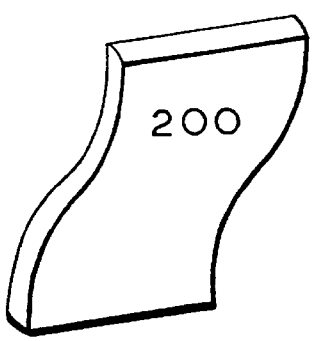
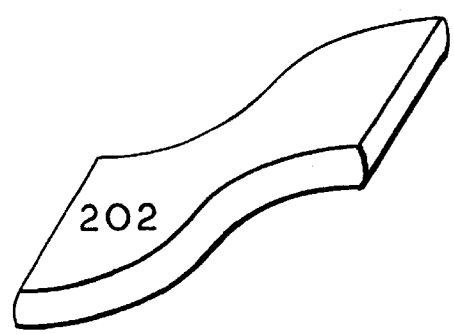
FIG. 10A

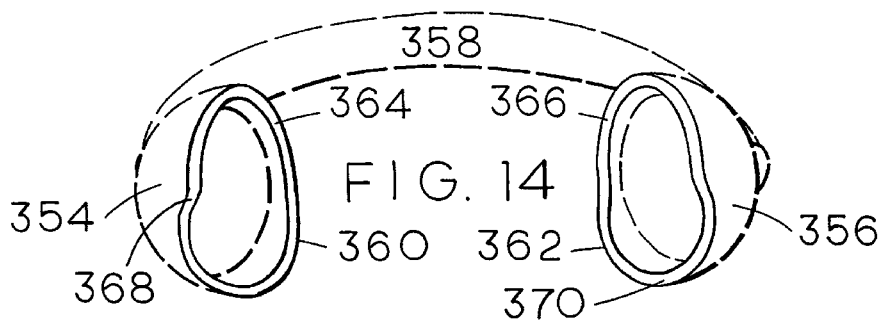
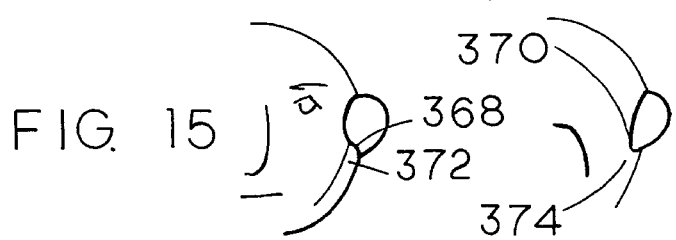
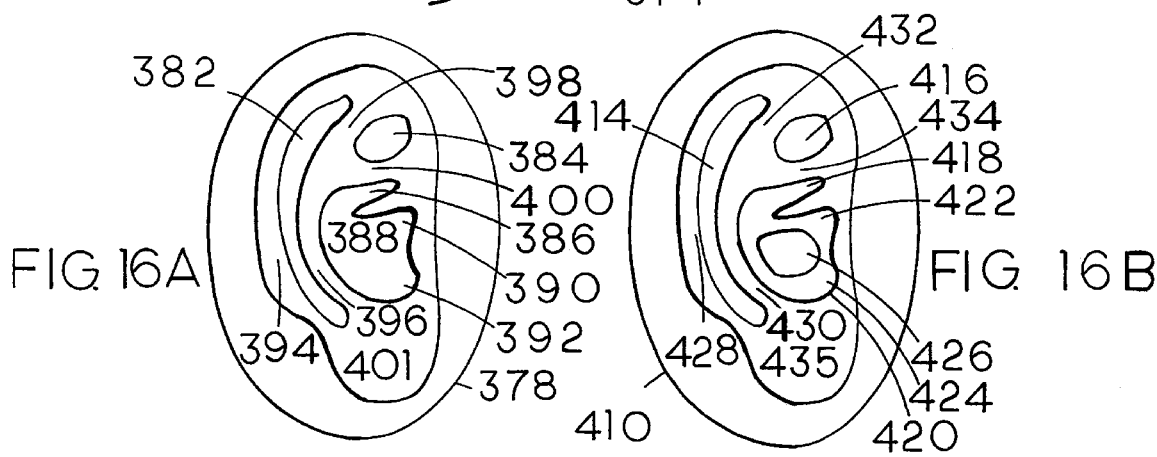
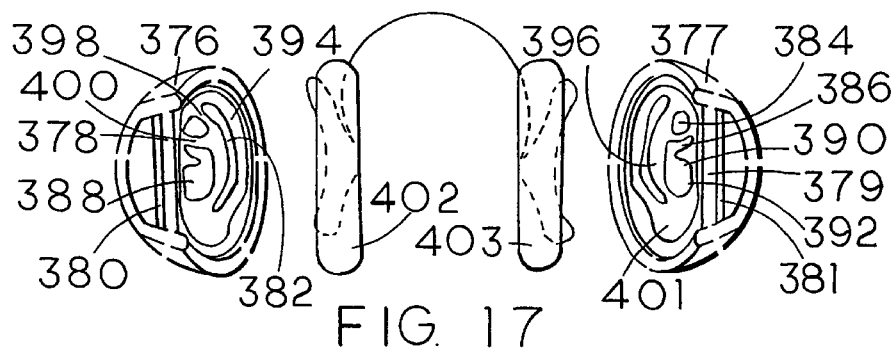

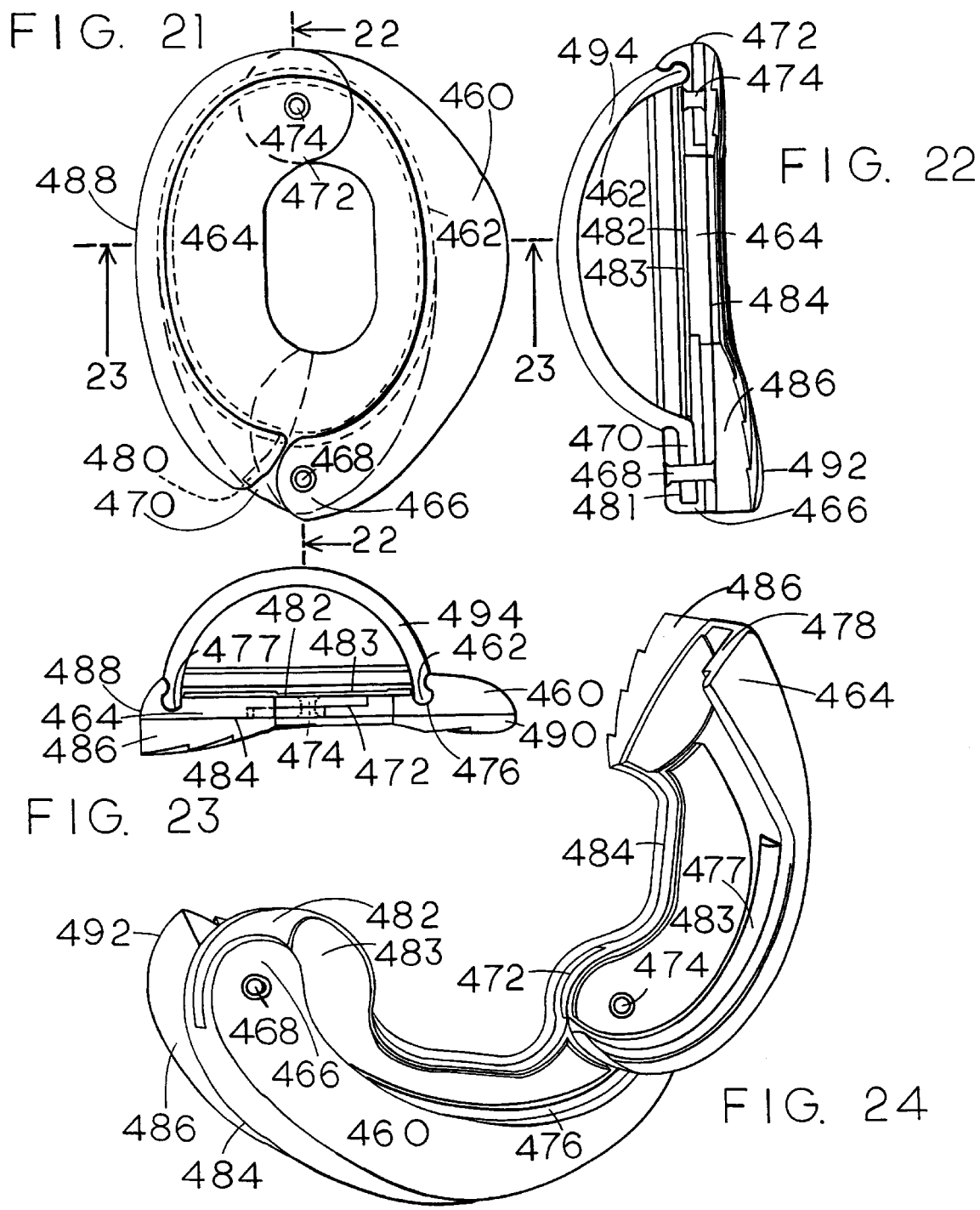

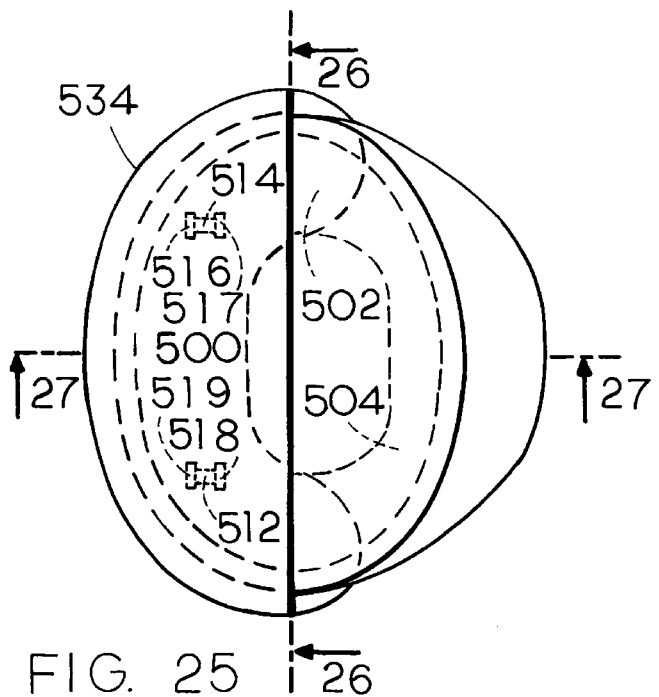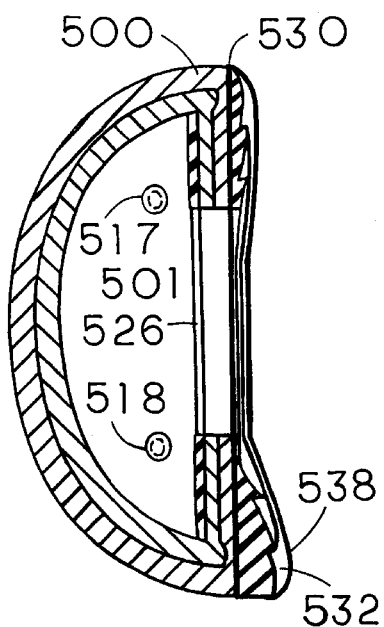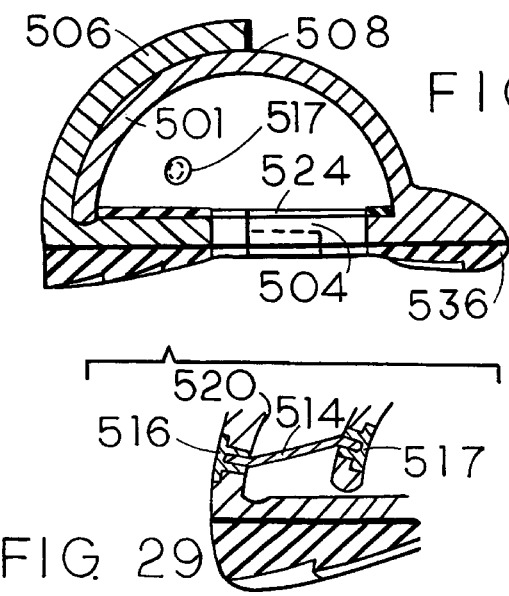

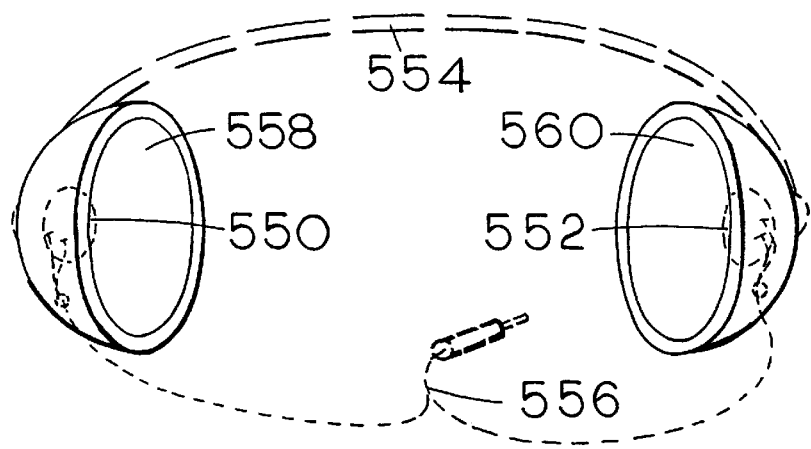
FIG. 30
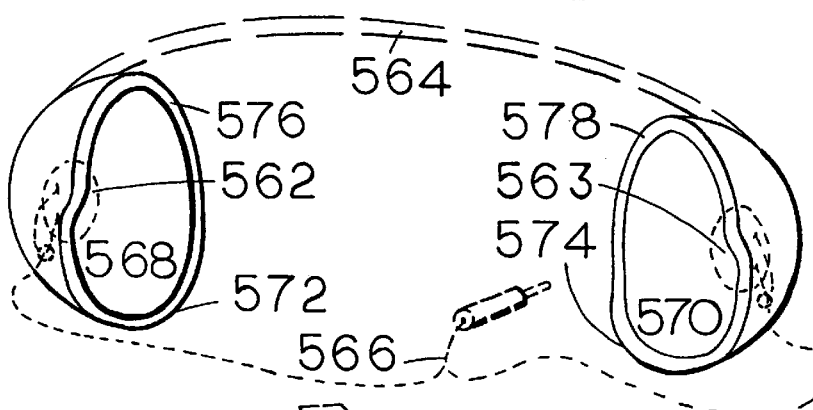
FIG. 31
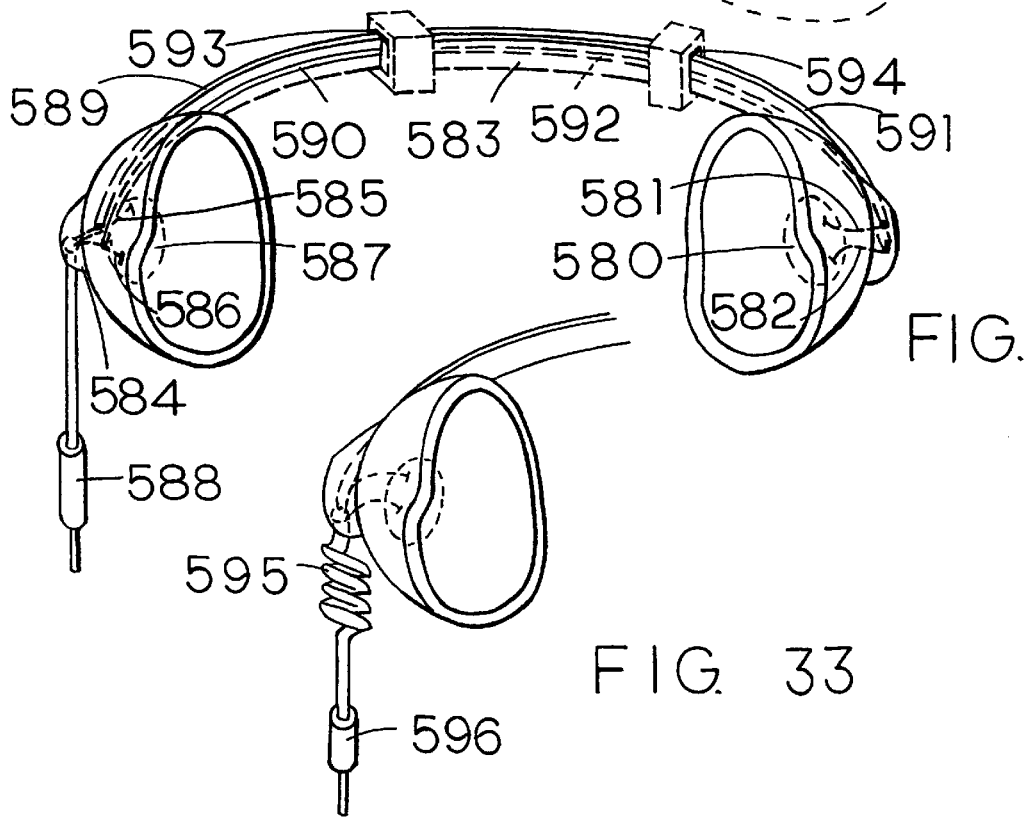
FIG. 32
FIG. 33

SOUND BAFFLING DEVICE

BACKGROUND OF THE INVENTION

This invention relates to the field of sound baffling devices, and more particularly the use of an enclosure containing a vacuum to baffle sound, as well as the various practical uses to which this invention may be put. Some other improvements which aid the invention in operation are also shown.

Sound baffling devices have been used in the past to modify acoustics and to reduce the ambient noise reaching the ears. Such uses have included acoustic baffles for lecture halls and theatres, sound proof partitions to reduce the ambient noise, and the sound baffling cups of ear protectors. The means whereby these previous sound baffling devices achieved these results were essentially through sound deflection or sound reflection, and through sound absorption.

Many previous sound baffling devices also may have had no facility for dynamically adjusting the ambient sound. If such facility was present, it may have involved a change in the spatial disposition of the sound baffling devices. The ability to dynamically alter the inherent sound baffling characteristics of sound baffling devices may not have been shown previously.

For sound absorption, cellular plastics were often used. These plastics have shown various spectral sound absorption characteristics. In general these plastics were comprised of either whole or fractured cells containing air. Hence these plastics were also capable of some sound transmission. However, although these plastics could be used as fillers, most auspiciously in the cavities of buildings, they do not appear to have had any previous use to baffle sound in this way.

In spite of the materials previously available, some previously known devices did not use sound baffling, even when such use would have been beneficial. In head phone sets, sound baffling cups were not used to baffle the ambient noise, even though transmitted noise considerably reduces the audibility and perceived rendition of the rendered sound.

Some previous ear protectors used sound baffling cups having openings which were elliptical or circular and resident in one plane. This, while workable, does not take into account the curves of the human body surface, and the fit is therefore less than optimal.

Some previous devices also used a semicircular fitting means which relies on elastic tension to hold the sound baffling cups against the ears. Because of the spatial requirements of the semicircle some head gear may not be comfortably worn when this type of fitting means is used.

Also, most previous head phone sets generally used a Y shaped wiring arrangement to reach the speakers of the respective ears. This wiring arrangement is less than optimum as it can interfere with the movement of the head and neck.

In most previous devices, the connection to the playback unit is made by means of a wiring arrangement to a plug-in connector which resides in the playback unit. If the connecting means of these devices is snagged, the connection has a tendency bind fast in the playback unit plug-in connector, thereby allowing considerable stresses to be applied to the connecting means.

SUMMARY OF THE INVENTION

Although the theory of operation and/or functioning of the invention is not fully understood, according to one of its aspects the invention comprises the use of an enclosure containing a vacuum to baffle sound. Although the invention may baffle sound by means of sound deflection, sound reflection, and sound absorption like some previous devices, the use of a vacuum improves on this. And a perfect vacuum, being substantially opaque to sound, should function as a total barrier to sound, although peripheral transmission and absorption along the enclosure may still take place.

Since a perfect vacuum should be opaque to sound, a perfect vacuum should function as a complete barrier to sound. In practice, the vacuum may not always be perfect. Hence there may be a small amount of transmission through the vacuum. However, if the degree of rarefaction of the matter within the enclosure is sufficiently great, this amount may be so small as to be negligible. Accordingly a vacuum may, in the context of this writing, be taken to mean rarefied matter, most particularly rarefied air or a rarefied gas or a mixture of rarefied gases. And a perfect vacuum may, in the context of this writing, be taken to imply the limiting condition of total rarefaction, in essence a space devoid of matter.

It is therefore an object of the invention to show how an enclosure containing a vacuum may be used to baffle sound. As said before, although the invention may be used with the intent of completely preventing the transmission of sound, there may still be peripheral transmission along the material of the enclosure. However, a proper choice of materials for the enclosure should minimize this, thereby allowing the invention to provide better and more efficient sound baffling than that provided by comparable devices. The increase in efficiency may be due to the saving in material. Since a vacuum may function as well over small dimensions as over larger dimensions it may be possible to reduce the size of the sound baffling device. Hence savings in size and weight may be realized over comparable devices.

It is a further object of the invention to show how a plurality of enclosures containing a vacuum may be used to comprise a large sound baffling device. A very large enclosure would probably require internal supporting struts to counteract the external pressure. A sound baffling device of equivalent size can be constructed from a cellular material comprised of a plurality of enclosures containing a vacuum. Such a material should not require supporting struts. Materials that may serve well for this purpose are glasses or plastics having a cellular structure. And porous materials may also be used, providing a suitable process for creating a cellular structure is applied to them. The process should seal the surface of the porous material, thereby creating the cellular structure and preventing the entry of ambient matter, which is usually comprised of air.

It is therefore a further object of the invention to show how materials having a porous structure may be processed to create a cellular material comprised of a plurality of enclosures containing a vacuum, so that the created cellular material is suitable for baffling sound. When the material is a naturally occurring material having a porous structure, it may be exemplified by pumice.

And it is still a further object of the invention to show how a plurality of the enclosures or of the created cellular material, containing a vacuum and dimensioned to be suitable for pouring can be used to fill holes and cavities. And the invention shows how the addition of a suitable binding agent may be used to create a composite cellular material that fills the holes and cavities to the substantial exclusion of all air voids between the cells or cellular material that is poured into the holes.

It is still a further object of the invention to show a process of manufacture for creating a composite cellular material. A suitable binding agent is mixed with a plurality of enclosures or a plurality of cellular material containing a vacuum. A shaping process as well as a catalyst may then be applied. Upon the completion of the process, the composite cellular material should be created.

It is therefore a further object of the invention to show how a cellular material comprised of enclosures containing a vacuum can be shaped to spatial specifications. This allows the shape of the sound baffling device to be customized. A material that may be used to this end is a cellular plastic. Or glass globules containing a vacuum may be embedded in a binding agent of nylon to comprise said cellular material. And naturally occurring materials such as pumice may be used as well, after undergoing a suitable method of refinement, which should include the sealing of the surface.

And it is still a further aim of the invention to show how enclosures having various geometries may be used. Although the vacuum is substantially opaque to sound, these geometries may all have different sound baffling capabilities because of the difference in the sound reflection and sound deflection characteristics of the different shapes, as well as the difference in the sound absorption of the material that may be applied to their surface. The two general geometries that are described are the solid geometry where the enclosure has considerable extent in all three dimensions and the plane geometry where the enclosure has substantially negligible extent in one of the dimensions and thus effectively functions as a hollow sheet or plane.

It is a further object of the invention to show how supporting struts may be used to counteract the external pressure for large enclosures. Because of the vacuum inside the enclosure, the enclosure may need to be reinforced against the external pressure.

And it is a still further object of the invention to show how the sound baffling characteristics of the invention may be varied by the admitting and removing of matter to and from the enclosure. Since a reduction in the vacuum may increase the transmission of sound through the enclosure, varying the matter within the enclosure may vary the sound baffling characteristics of the enclosure. Generally this is done by admitting or removing air from the enclosure.

And it is a still further object of the invention to show how a controlling means may be used to achieve an optimum correspondence between ambient or acoustic properties of sound chosen by means of parameters entered into said controlling means, and the ambient or acoustic properties of sound measured within the physical space governed by said controlling means.

It is therefore a further object of the invention to show how a vacuum chamber connected to the means for admitting and removing of matter may be used to speed up the admitting and removing of matter from the enclosure. In general the matter will be comprised of air or a gas or a mixture of gases.

And it is a still further object of the invention to show how manufacture may take place inside a vacuum chamber. By manufacturing inside a vacuum chamber, the process of creating the vacuum in the enclosure is eliminated, and this may simplify the construction of an enclosure containing a vacuum in some cases.

From the aspects summarized thus far, it is clear that the invention may have many uses. It is therefore a further aim of the invention to show how it may be used to create sound proof walls and ceilings, or bricks and building blocks substantially impervious to sound, or the sound proofing of holes or gaps within structures, or the creation of sound proof casings for industrial equipment, or the creation of sound proof structural components, or the creation of moveable sound proof dividers or partitions, or the sound proofing of vehicular bodies, or the controlling of acoustic characteristics, or the creation of directional speakers.

Most specifically, according to another of its aims the invention comprises the use of sound baffling cups to reduce the ambient noise reaching the ears. When included in sound baffling cups, the vacuum should provide better reduction of the ambient noise than that provided by some previous devices. Although previous devices, such as ear protectors, used sound absorption or sound deflection or sound reflection to achieve a reduction in the ambient noise, the use of sound baffling cups in combination with head phone sets does not appear to have been used in any previously known device.

It is therefore an object of the invention to show how the combination of sound baffling cups with head phone sets may be used to reduce the ambient noise and improve the audibility and perceived rendition of the rendered sound.

And it is a further object of the invention to show how the combination of head phone sets and ear protectors with sound baffling cups incorporating a vacuum may be used to reduce the ambient noise and improve the audibility and perceived rendition of the rendered sound.

It is still a further object of the invention to improve the comfort and fit of head phone sets and ear protectors by adding a lip contour complementing the shape of the head and neck to the sound baffling cups of head phone sets and ear protectors.

It is still a further object of the invention to improve the comfort and fit of ear protectors and head phone sets by eliminating and replacing the semicircular elastic fitting means used in some previous devices with a complementary contour or cushioning material fashioned to complement the shape of the external ear and having a latching means for holding the complementary contour or cushioning material against the external ear. One material used for the complementary contour or cushioning material may be foam rubber. By using a complementary contour or cushioning material, both ear protectors and head phone sets using sound baffling cups become more comfortable and less cumbersome. This may be improved further by using a mould made from the external ear to customize the complementary contour. This should produce a device having a tailored fit, which may by improved still further by making the complementary contour or cushioning material from a material having a binding preference for skin.

It is therefore still another object of the invention to show how the latching means may be comprised of a jointed clip having two parts. The latching means rotates to fit in between the external ear and the head and neck, thereby pressing the external ear laterally into the complementary contour or cushioning material as the case may be.

And it is still a further object of the invention to show how the latching means may be comprised of a lune shaped sliding clip having an arc shaped flange. The sliding clip is attached to the posterior half of the sound baffling cups by a holding means. By pulling the sliding clip backwards to fit in behind the posterior part of the external ear, the sound baffling cups may be latched against the external ear.

It is still another object of the invention to make the connecting means of the head phone sets less obtrusive. By running the connecting means from one speaker to the other speaker and from there on to the playback unit, the Y shaped wiring arrangement is eliminated because only one path is used, thereby making the connecting means less obtrusive.

It is still another object of the invention to show how stresses placed on the sound baffling cups of head phone sets having a single path connecting means may be eliminated by the use of a helical wiring arrangement. The helix effectively functions as a spring absorbing the head and neck motion.

It is a still further object of the invention to show how the arc-shaped metal bands of some of the prior art may be replaced by elastic hollow tubular segments. The tubes are connected to enable the smaller tubes to slide fixedly within the larger tubes. The connecting means which connects the speakers of this embodiment to the playback unit may also be configured to follow a single path, thereby eliminating the Y shaped wiring arrangement of some previously known head phone sets.

It is still another object of the invention to show how to reduce the excessive strains which caused the quality of the connecting means to be degraded in some previous devices. The invention does this by moving the plug-in connector to a more favourable position within the connecting means, thereby allowing the connecting means connection to be pulled from the plug-in connector if a snag or bind occurs, and so reducing the amount of stress to which the connecting means is subjected.

A modification for reducing the stress applied to the Y-shaped connecting means of some previously shown head phone sets shows how the connecting means connection may be moved to the fork of the Y. Connection to the playback unit is then made by means of an automatically retractable playback unit extension.

BRIEF DESCRIPTION OF THE DRAWINGS

1. FIG. 1 shows a sound baffling device containing a vacuum.

2. FIG. 2 is a cutaway drawing showing the interior of the sound baffling device shown in FIG. 1.

3. FIG. 3 shows an sound baffling device comprising a plurality of enclosures. The hatched outlines refer to those sides of the enclosures which are located within the body and to the rear of the plurality.

4. FIG. 4 shows the sound baffling device of FIG. 3 while showing only the hatched outlines of the hidden cell.

7. FIGS. 7A, 7B and 7C shows the group of enclosures that are selected from a sphere, a hemisphere, a zone and segment of one base, a zone and segment of two bases, a spherical sector, a lune, a cylinder, a cone, an elliptic paraboloid, a hyperboloid of one sheet, a hyperbolic paraboloid, an ellipsoid, a torus, a pyramid, a moebius strip, a klein bottle, a handle, a concave polyhedron, or a convex polyhedron.

8. FIG. 8 shows the group of enclosures selected from a tetrahedron, a hexahedron, an octahedron, a dodecahedron, or an icosahedron and also shows the group of enclosures selected from a prism or an antiprism.

9. FIG. 9 depicts an enclosure formed like a hollow sheet and shows that the upper and lower surfaces of said sheet may have an irregular shape.

10. FIGS. 10A, 10B, 10C, 10D and 10E shows the group of enclosures shaped with a two dimensional curvature corresponding to curves defined in the xy plane.

14. FIG. 14 shows the lip contour which may be applied to the lips of sound baffling cups and the medial side of some of the latching means.

15. FIG. 15 shows how the lip contour fits the human body surface in the region of the head and neck.

16. FIGS. 16A and 16B show the complementary contours that should be used for ear protectors and head phone sets respectively.

17. FIG. 17 shows how the latching means and the complementary contours that should be used for ear protectors combine with the sound baffling cups of previously known ear protectors.

21. FIG. 21 shows the jointed clip in a closed position and attached to one of the sound baffling cups. The view is taken medianly through a sagittal plane.

22. FIG. 22 is an anterior cross section of the view shown in FIG. 21. It displays some of the lip contour applied to the bracing material that is attached to the medial surface of the jointed clip.

23. FIG. 23 is an inferior cross section of the view shown in FIG. 21. It draws attention to the wedge shape of the jointed clip.

24. FIG. 24 is a separate view of the jointed clip. It shows the jointed clip in an opened position so as to give a better view of the grooves and tongues etc.

25. FIG. 25 shows the sliding clip in a closed position and attached to one of the sound baffling cups. The view is taken laterally through a sagittal plane.

26 FIG. 26 is an anterior cross section of the view shown in FIG. 25. It illustrates how the posterior part of the sound baffling cups is contained within the sliding clip. It also displays some of the lip contour applied to the bracing material that is attached to the medial surface of the sliding clip.

27. FIG. 27 is an inferior cross section of the view shown in FIG. 25. It draws attention to the wedge shape of the sliding clip and shows how the elastic material of the holding means is attached.

28. FIG. 28 is a separate view of the sliding clip and attempts to give a better view of its shape.

29. FIG. 29 is a close up view of the holding means showing the elastic material and the holding plates attached to the sound baffling cup and the sliding clip.

30. FIG. 30 shows the combination of previously used sound baffling cups with head phone sets.

31. FIG. 31 shows the combination of sound baffling cups having a lip contour with head phone sets.

32. FIG. 32 shows an improved connecting means for head phone sets with sound baffling cups. The improvement combines the two branches of the connecting means which previously depended from the sound baffling cups into one branch.

33. FIG. 33 shows the single path connecting means of FIG. 27 with an improvement. The first section of the single path has a helical shape for stress absorption.

DESCRIPTION OF THE PREFERRED EMBODIMENT

Although the theory of operation and/or functioning of the invention is not fully understood, as shown in FIG. 1 according to one of its aspects the invention comprises a sound baffling device having at least one enclosure (52) containing a vacuum (56), such that the transmission of sound through said sound baffling device is substantially barred by said vacuum.

Figure 13:
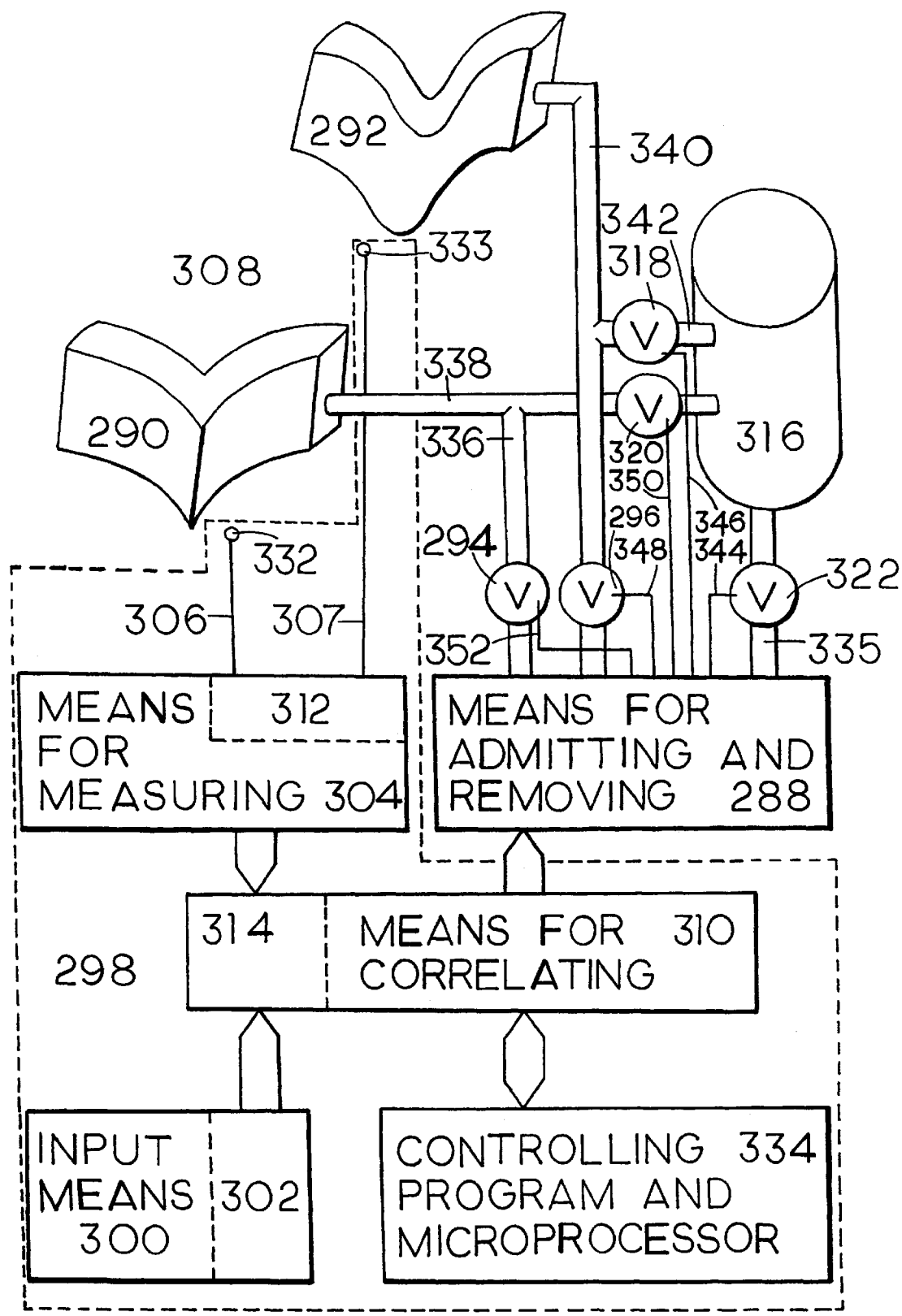
FIG. 13 shows the drawing of the preferred embodiment. It illustrates how a large scale arrangement of enclosures may be combined to comprise an sound baffling device and how this sound baffling device may be used in conjunction with a controlling means having a controlling program and a microprocessor. The sound baffling device shown in this drawing should be capable of dynamically controlling the ambient sound.

The cutaway view of FIG. 2 expands on this. A cross section of the walls of the enclosure is shown as well as a glimpse of the interior. In operation, the vacuum is contained and preserved by the walls (54) of the enclosure. Initially the vacuum may be created by removing matter within the enclosure by means of a valve (FIG. 13) located in or attached to the walls of the enclosure. This procedure should be used when the enclosure is constructed for connection to a controlling means. It may allow not only the removal of the matter from within the enclosure but also allows the matter to be returned to the enclosure should this be desired, as may often be the case where a controlling means is connected to the enclosure. In most cases the matter will be air or a gas or a mixture of gases. However it may sometimes be preferable to use a liquid to achieve specialized sound baffling characteristics.

Alternatively, the vacuum may be created within the enclosure by constructing and sealing an enclosure within a vacuum chamber. This method of construction maintains substantially constant sound baffling characteristics for the enclosure and is preferable when these types of characteristics are required. The type of construction may be substantially the same as that used for the creation of vacuum chambers and vacuum bottles or containers by previously used engineering methods. Or the enclosure may be constructed within the vacuum chamber by taking preformed walls or sides and joining them, preferably with interlocking joints, to comprise the enclosure. A suitable sealant is then applied to seal the joints so that the vacuum may be preserved against ambient matter. Such a sealant would preferably be a silicone or epoxy sealant.

Because sound requires a medium for transmission, it seems reasonable to suppose that the absence of a medium may prevent the transmission of sound. Accordingly, the invention comprises different embodiments of sound baffling devices each having an enclosure or plurality of enclosures containing a vacuum. Fundamentally, some of these different embodiments may be created by simply changing the shape of the enclosure. Alternatively, further embodiments may be created by aggregating the enclosures in spatial combinations as exemplified by the clusters of acoustic baffles in a theatre or lecture hall. Or the spatial combinations may be contiguous as in a wall constructed from bricks having the enclosures containing a vacuum within them.

Therefore, as shown in FIG. 4 according to one of its aspects the invention comprises a plurality of enclosures (88, 90, 92, 94, 95, 96, 98, 100), wherein each enclosure is a cell containing a vacuum, such that said plurality of enclosures comprises a material having a cellular structure (FIG. 3 or 4), so that the transmission of sound through said material is substantially barred by the vacuum (as in FIG. 2, 56) contained in the cells of said material.

The cellular material shown in FIG. 3 is comprised of eight cells. These cells are shown numbered in FIG. 4, wherein the hatched lines indicates the space occupied by the hidden cell (95). A larger section of cellular material may have many more cells. Furthermore the cells in FIG. 3 are not drawn to scale and may actually be much smaller than would be indicated by the dimensions of the drawing.

The walls and edges of these cells are also shown in FIG. 3. The dashed lines indicate the edge boundaries between the cells. Cell (FIG. 4, 88) has a spherical shape and shares walls with the cylindrically shaped cell (94), the irregularly shaped cell (90), the block shaped cell (92), the further irregularly shaped cell (98), the loaf shaped cell (96), and the hidden cell (95) of the lower left rear corner of the plurality.

The hidden cell may be also be discerned by consulting FIG. 3. The base of the cell is defined by edges 80, 82, and 84. The three rear sides of the cell are defined by edges 64, 60, 62, edges 60, 58, 82, and edges 58, 72, 74, 78, respectively. Edges 70, 74, 76 and that part of edge 86 which lies above the intersection of edge 86 with edge 76 define the wall which the hidden cell shares with cell 98. Edges 76, 78, 80 and that part of edge 86 which lies below the intersection of edge 86 with edge 76 define the wall which the hidden cell shares with cell 100. Edges 64, 84, 86 and 68 define the wall which the hidden cell shares with cell 94. And edges 62, 68, 70, 72 define the wall which the hidden cell shares with cell 96.

The advantage of this cellular material is that is allows the construction of a large sound baffling device that should require no internal supporting struts for the enclosures. Because of the external pressure that may act on the enclosure, for large enclosures internal supporting struts may be required. This requirement may depend on the strength and shape of the material of the enclosure as well as on the external pressure. However for a sufficiently small enclosure the inherent strength (the ability to resist external pressure) of the enclosures may show an increase proportional to the decrease in size, and the enclosures may therefore be able to resist the external pressure and maintain structural integrity without supporting struts.

Many materials may show this proportional increase in inherent strength with decreasing scale, among them the glasses and the plastics. It may therefore be preferable that the cellular material is formed from enclosures comprised of glass so that said material is a glass having a cellular structure. A way of constructing such a material may be found by placing a form filled with glass globules containing an vacuum inside a vacuum chamber which is evacuated. Heat is then applied causing the walls of the glass globules to coalesce through partial melting, thereby forming common walls. In this way, upon cooling a cellular material comprised of glass may be created.

The same procedure may be applied to plastic globules containing a vacuum. Depending on the plastic used and the process desired, heat or a catalyst or an adhesive sealant may be applied to the plastic globules. This may cause the walls or boundaries of the plastic globules to coalesce through partial melting or bonding, thereby forming common walls. In this fashion a cellular material comprised of plastic and containing a vacuum may be created.

As is well known, a further way in which a cellular plastic may be created is by mixing a molten thermoplastic material with a gas or liquid which is volatile at normal atmospheric pressure and subjecting the mixture to elevated temperature or pressure in a closed chamber. The material is then released from the closed chamber through a suitable die opening, thereby releasing the pressure and causing the gas to expand. This results in a permanent porous or cellular plastic upon cooling. If in addition the die opening is connected to a vacuum chamber, then when the vacuum chamber is evacuated concurrently with the expansion of said material, a vacuum may be incorporated into the cells of said material. This vacuum may be preserved against the action of ambient matter by incorporating a bitumen or other sealing agent into the thermoplastic material. Or the vacuum may be preserved by applying a suitable sealant to finished units of said thermoplastic material before removal from the vacuum chamber. For expandable polystyrene or polyurethane such a sealant may be a urethane or epoxy sealant. It may therefore be preferable that the cellular material is formed from enclosures comprised of plastic so that said material is a plastic having a cellular structure.

Figure 5:
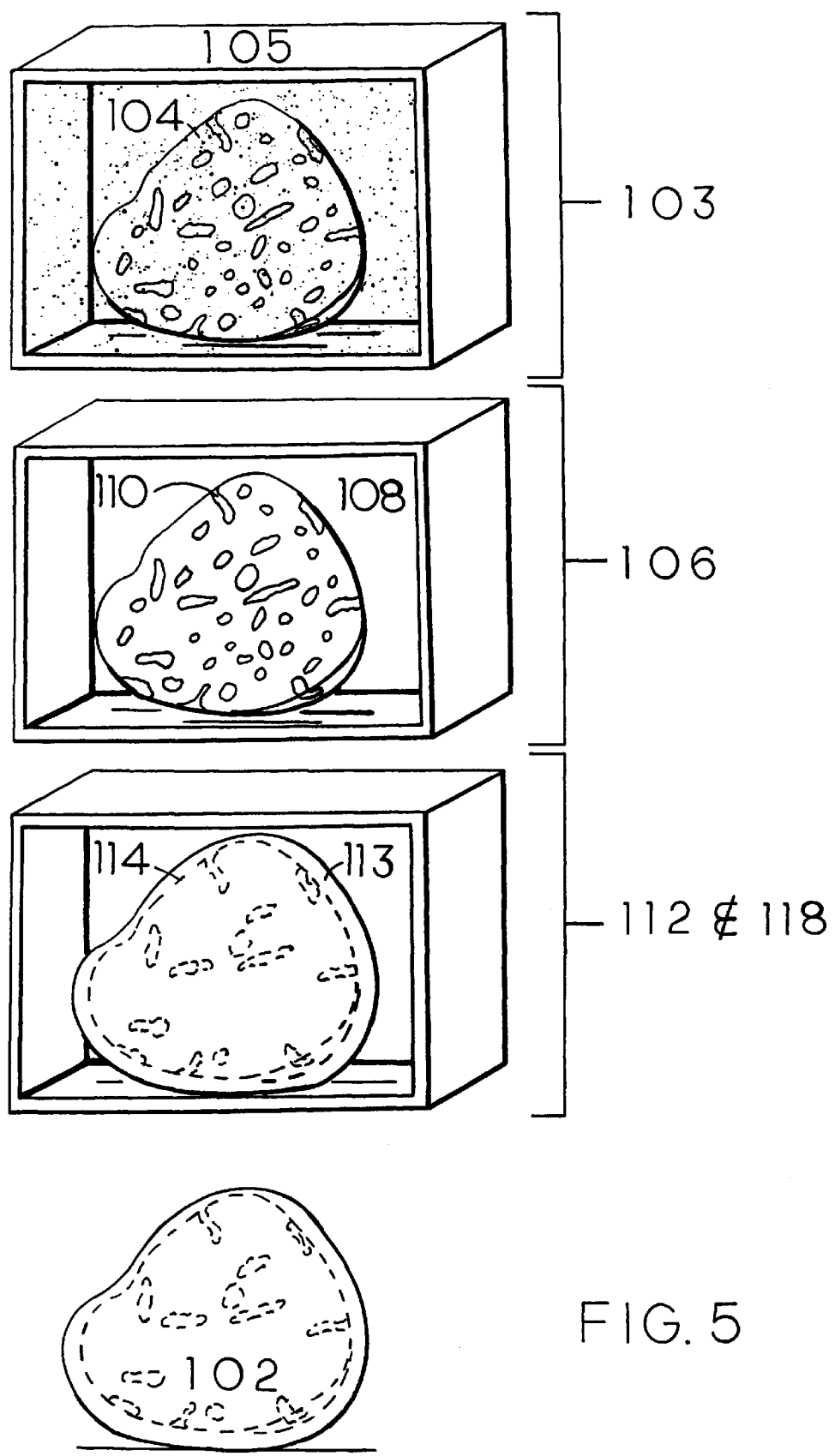
FIG. 5 shows the first process of manufacture that uses a material having a porous structure to create a cellular material.

A first process by which a material having a cellular structure can be created is shown in the sequential views of FIG. 5 which illustrates that the invention comprises a first process of manufacture that uses a material having a porous structure to create the material having a cellular structure (102), said first process having the following steps in the sequence set forth;

The first step (103) in the first process of manufacture comprising the placing of said material having a porous structure (104) within a vacuum chamber (105), The second step (106) in the first process of manufacture comprising the creation of a vacuum (108) within said vacuum chamber, so that after a suitable interval of time said vacuum extends substantially throughout the porous structure (110) of said material, The third step (112) in the first process of manufacture comprising the application of a sealant (113) to the surface (114) of said material such that the vacuum is incorporated within said porous structure and is preserved against contact with ambient matter, The fourth step (118) in the first process of manufacture comprising the application of a suitable curing process when necessary, so that after the completion of said first process of manufacture the material having a cellular structure (102) is created.

The porous structure of the material used in the first process may be comprised of tubular openings to the surface or microscopic transport apertures that allow the air to escape when the material is exposed to the vacuum within the vacuum chamber. (The vacuum chamber is represented by the cross-sectional view of the box in FIG. 5.) In step 2, the transport of the air (The air is indicated by stippling in the illustration of the first step (103) of FIG. 5.) from the porous material and out of the vacuum chamber upon the creation of the vacuum does not have to be instantaneous. If it is not, a reasonable length of time is allowed for the air to transport out of the material upon application of the vacuum. When the transport is completed the surface of the material is sealed with a suitable sealant. For example, when the material is a porous plastic a suitable sealant may be a properly admixtured epoxy resin. Or a urethane sealant may also be used.

The sealing of the surface may also involve a suitable curing process as defined in step 4. But, especially when the sealant is fast setting and the surface is sealed more or less instantaneously, this may not always be necessary. For thermosetting plastics the curing process should involve the application of heat and may or may not involve a chemical catalyst. For some materials it may merely involve waiting for the sealant to harden and any excess vapour to be drawn off.

It follows that the porous material need not be plastic but may also be metal, glass, or any other suitable material. It may therefore be preferable that said material having a porous structure is a naturally occurring material having a porous structure. Such naturally occurring materials may be both organic and inorganic. Among the organics we find the sponges and among the inorganics we have materials such as pumice. It may therefore be preferable that said naturally occurring material having a porous structure is pumice. The pumice is brought into the vacuum chamber and then the chamber is evacuated. After the ambient matter has been substantially removed from the cells of the pumice the surface of the pumice is sealed in the presence of the vacuum. Although it appears at first glance that polysulfide sealants may be used, they are known to degrade somewhat when in contact with a vacuum due to outgassing etc. This may, if the exposure of the polysulfide sealant to the vacuum is significant, compromise the sealing function. In general, sealants that are known to have a high risk for degradation upon contact with a vacuum, are the acrylics, polyamides, polysulfides, and neoprenes. It is therefore preferable that the sealant be selected from a group that may in general function reliably in contact with a vacuum, notably the epoxies, urethanes, and silicones. For the sealing of pumice a silicone caulking or sealant composition may therefore be preferable.

The objective which is attained by the application of the sealant in the first process of manufacture for creating a cellular material is the preservation of the incorporated vacuum against any influx of ambient matter. This ambient matter may be a particulate, a liquid, a gas, or the air of the atmosphere. It may therefore be preferable that the ambient matter be air.

According to a further aspect the invention comprises a plurality of enclosures containing a vacuum, or a plurality of the material having a cellular structure that has been created by the first process of manufacture for creating a material having a cellular structure, so that said enclosures or said cellular material are dimensioned to comprise a product having a size and shape suitable for pouring (FIG. 6, 120), such that said product may be poured into holes and cavities, so that the transmission of sound through said holes and cavities is substantially reduced.

The most obvious area of application for this embodiment should be the construction industry. Various kinds of buildings may have holes, gaps, spaces or voids that can admit ambient noise. These gaps may be filled by pouring the enclosures into them. Although it may be preferable that the enclosures are glass globules, the enclosures may also be made of plastic, metal, or any other material that can be fashioned to this purpose. Furthermore, in filling these voids within buildings, the enclosures should also aid materially in improving the insulating properties of the structures.

Inherent insulating properties may be a general advantage of any of the enclosures, whether part of a cellular structure or not. For a large autonomous enclosure, the addition of a suitable reflective coating to the inside walls of the enclosure should substantially reduce the transmission of heat by means of infra red radiation. Although reflective coatings may have been used previously to reduce the transmission of infra red radiation, their use in building blocks, bricks, or structural components containing a vacuum may be new. Hence, if the invention is used with this end in mind, both maximal sound proofing and insulating characteristics may accrue to materials or components which also incorporate the reflective coating.

Although the enclosures dimensioned to comprise a product suitable for pouring may be loosely poured into requisite holes, gaps or spaces it is also possible to add a suitable binding agent to fill in the air voids between the enclosures. For example, using a nylon filler in conjunction with glass globules containing a vacuum would allow the creation of a mixture for the elimination of air voids. Such a mixture may, after applying a suitable catalyst when necessary, set to form a material having a cellular structure. And this material should have a shape conforming to the holes, gaps, spaces, or voids within which the enclosures are poured, in effect functioning as a filler insulator and sound baffling material. Accordingly it may be preferable that the invention is comprised of a plurality of the product having a size and shape suitable for pouring and having a spatial distribution within a hole or cavity, said plurality further having a suitable binding agent added to form a mixture within said hole or cavity, so that said binding agent and said plurality form a cellular material within said hole or cavity.

Figure 6:
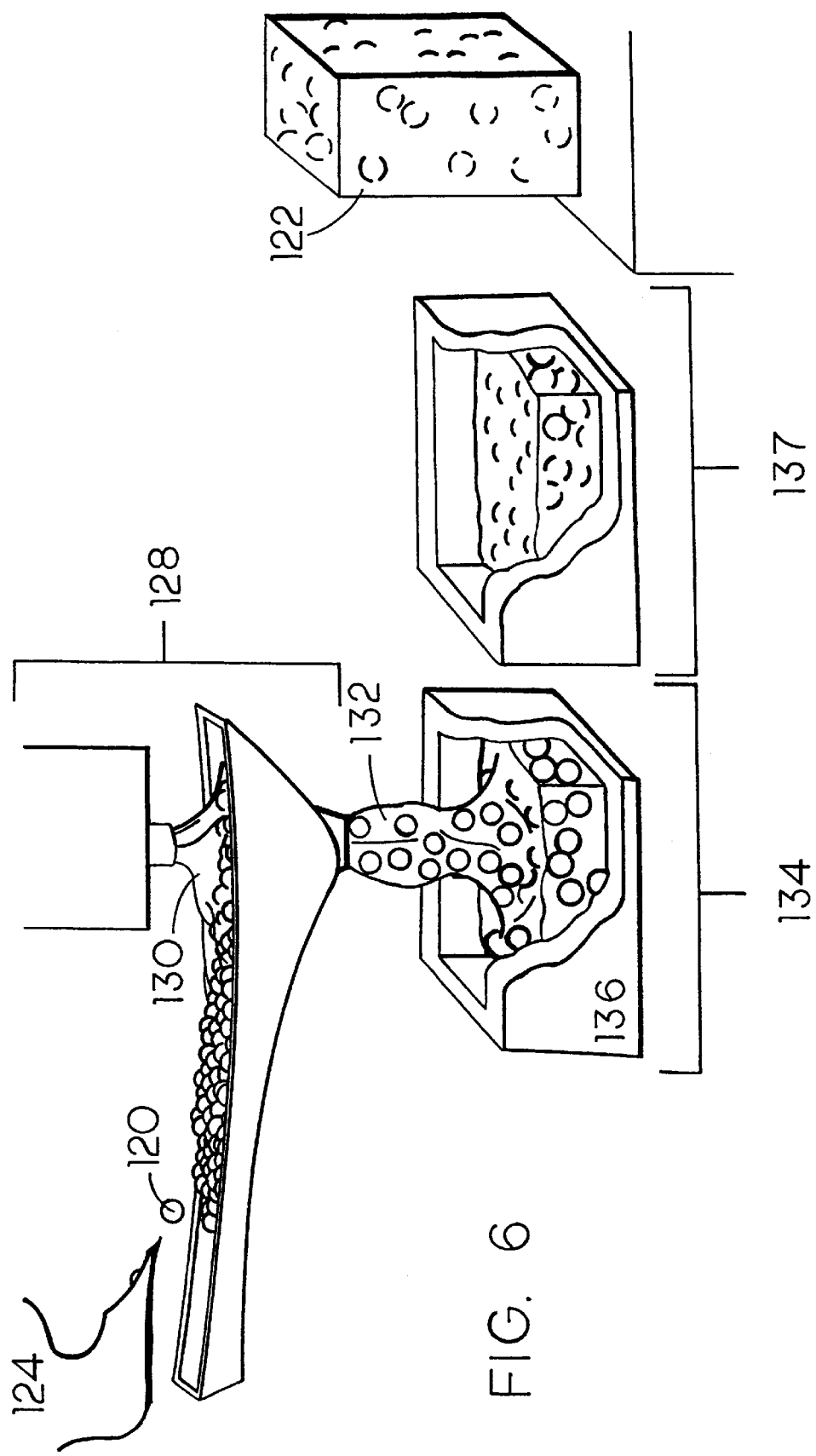
FIG. 6 shows the second process of manufacture that uses a pourable product to create a composite cellular material.

As shown in FIG. 6 according to another of its aspects the invention is comprised of a second process of manufacture that uses the product having a size and shape suitable for pouring to create a composite cellular material, said second process having the following steps in the sequence set forth;

the first step (124) in the second process of manufacture comprising the creation of said product (120), the second step (128) in the second process of manufacture comprising the addition of a suitable binding agent (130) to said product, such that said binding agent and said product form a mixture (132), the third step (134) in the second process of manufacture comprising the application of a shaping means (136) to said mixture, such that said mixture assumes a preferred shape, the fourth step (137) in the second process of manufacture comprising the application of a suitable curing process when necessary, so that a composite cellular material (122) is created upon the completion of said second process of manufacture.

This second process of manufacture shows how to create a composite cellular material from independently created enclosures and/or how to create a composite cellular material from blocks of cellular material created by the first process of manufacture. The independent enclosures or the blocks of cellular material are first combined with a suitable binding agent. A suitable shaping means is then applied. When the product used is comprised of plastic, this may be any one of the known methods of centrifugal casting, injection moulding, contact moulding etc. A curing process may then follow when necessary. For example, when using an epoxy resin with a product comprised of plastic a fatty amine curing agent may be used.

The binding agent used may also be a plastic which may or may not require a catalyst, retardant, accelerator, etc. It may therefore be preferable that the binding agent for said product is a plastic in combination with the catalyst required for said second process of manufacture. The catalyst is optional depending on the plastic. For thermosetting plastics it may simply be heat.

Alternatively, the product may simply be a plurality of glass globules, to which is added a binding agent comprised of glass fibres. The glass globules and the fibres may fuse under the application of heat. It may therefore be preferable that the product used in said second process of manufacture is comprised of glass globules containing a vacuum. It is a simple matter to use a plastic resin in conjunction with the glass fibres. This may produce a cellular material comprised of fibre glass having the glass globules embedded within it.

If glass globules are used an appropriate binding agent may also be nylon 6/6. For example, when contact moulding is used, generally a gelatin coat resin is laid up against a polished and waxed mould. The nylon laminating resin and the glass globules are then laid on. Also heat may be used as a catalyst to accelerate this process. It may therefore be preferable that said binding agent is nylon and the enclosures are glass globules containing a vacuum.

If a material having a cellular structure created from pumice is used, then the appropriate binding agent may be more of the sealant used to seal the pumice. This may comprise adding more of a silicone based caulking or sealant composition. Or it may be comprised of a further binding agent and/or filler which may also be mixed with a suitable catalyst.

Another advantage of using a cellular material containing a vacuum is that for some embodiments the material may be milled to specification without loosing the ability to baffle sound. This is because only those cells which are at the surface being milled loose the ability to baffle sound, due to rupture being induced by the milling process. It may therefore be preferable that the invention is comprised of a cellular material or composite cellular material that is workable, so that it may be shaped to spatial specifications.

Figure 7A:
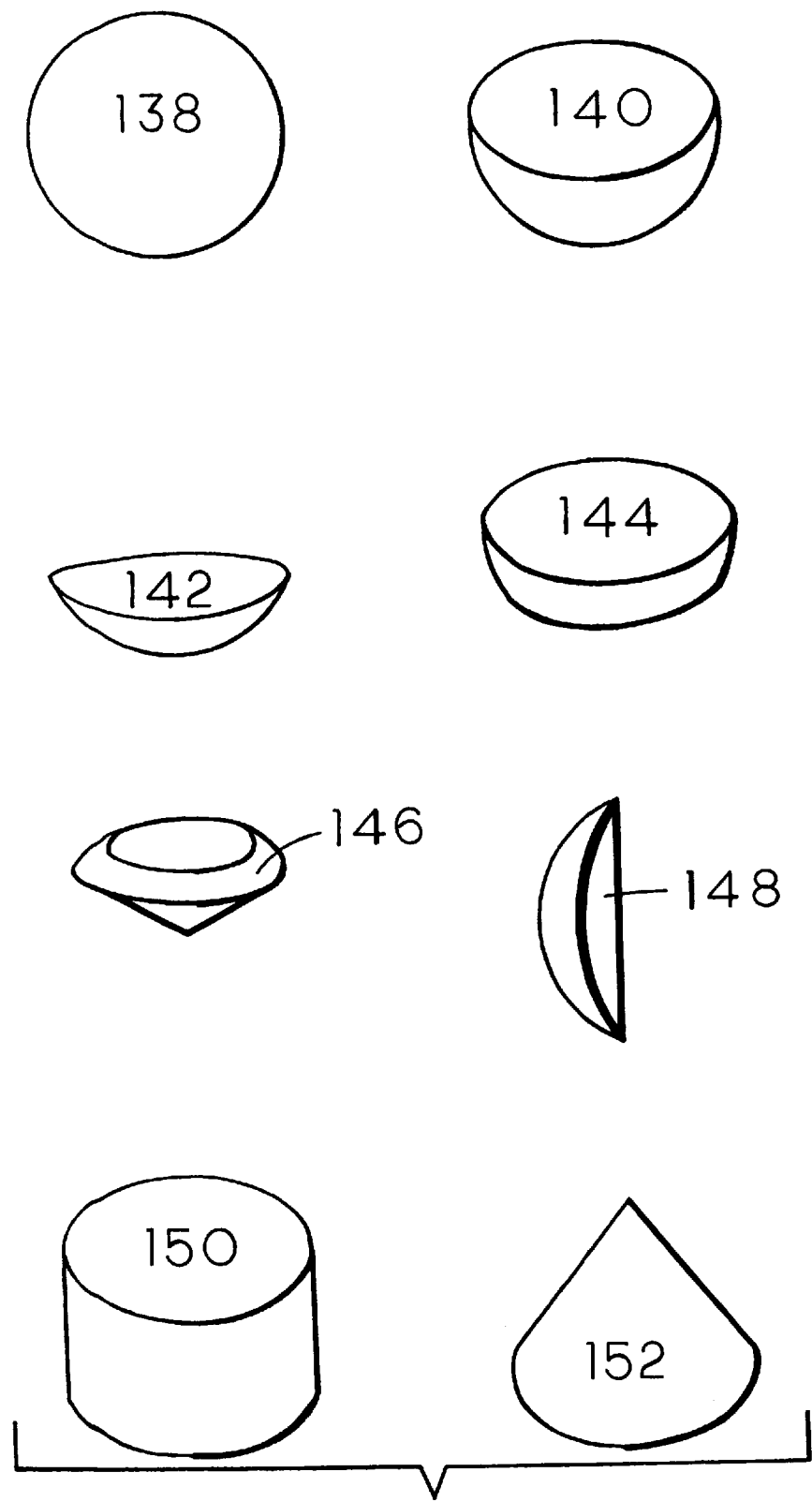
Figure 10B:
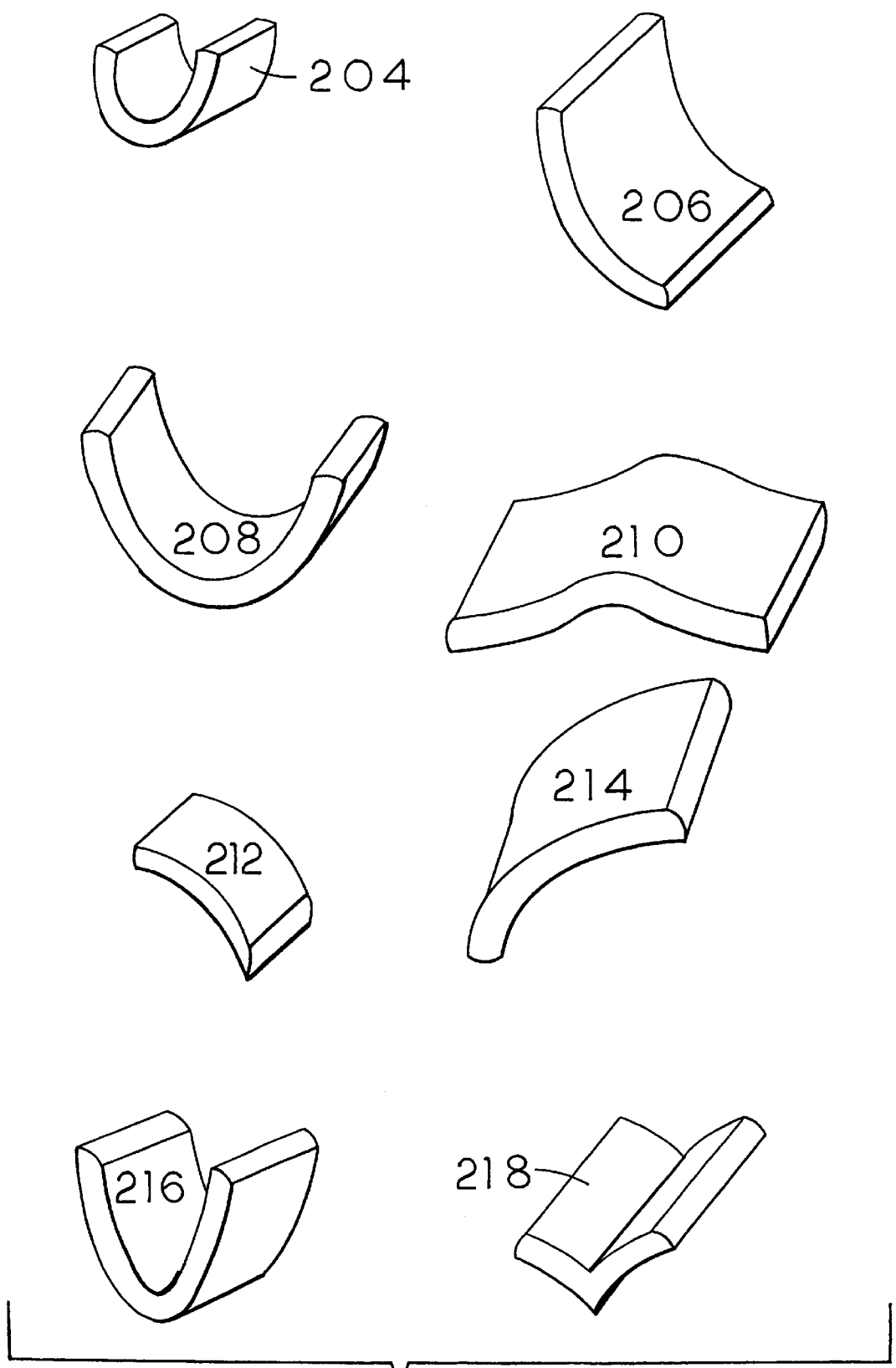
Figure 10C:
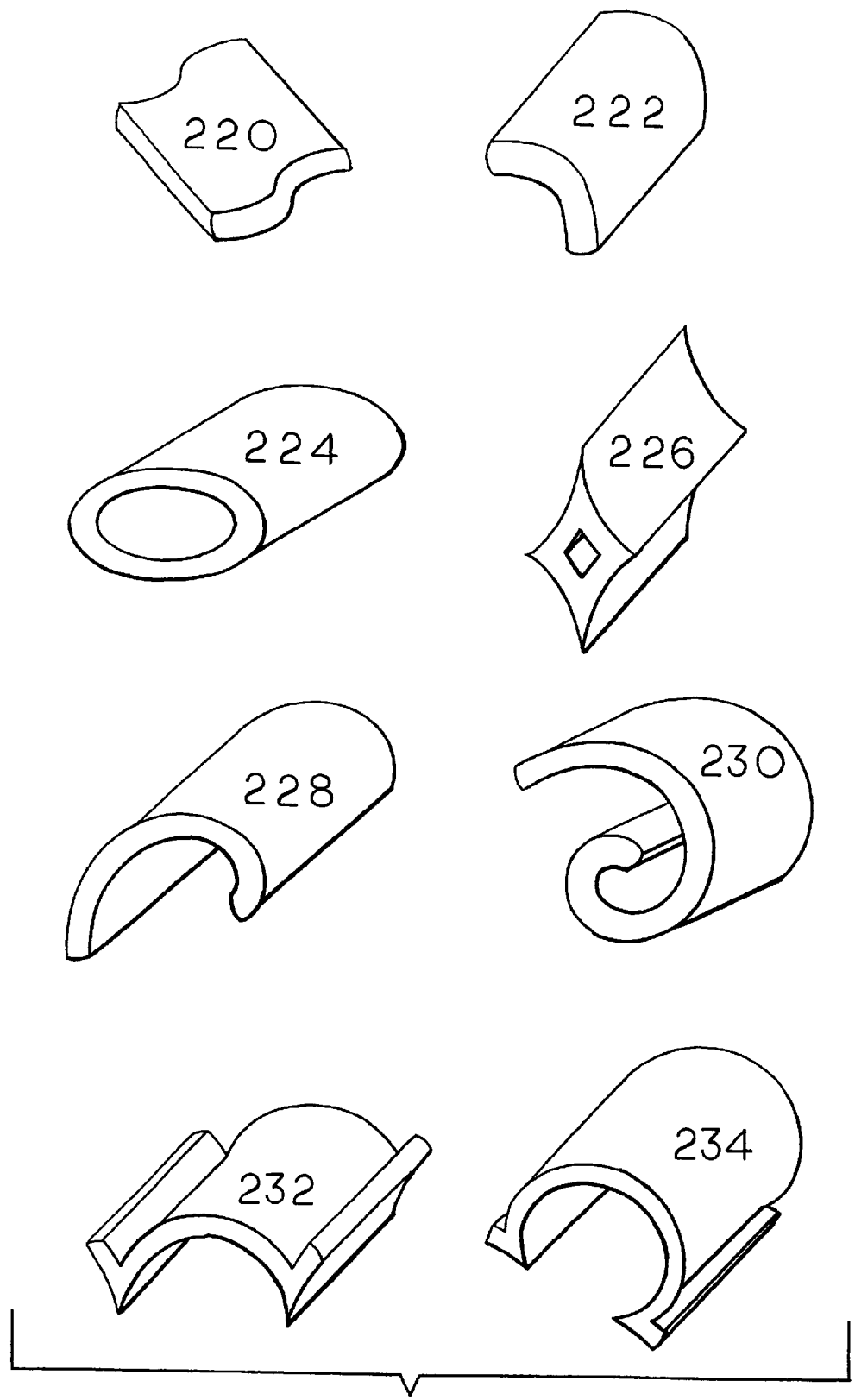
Figure 10D:
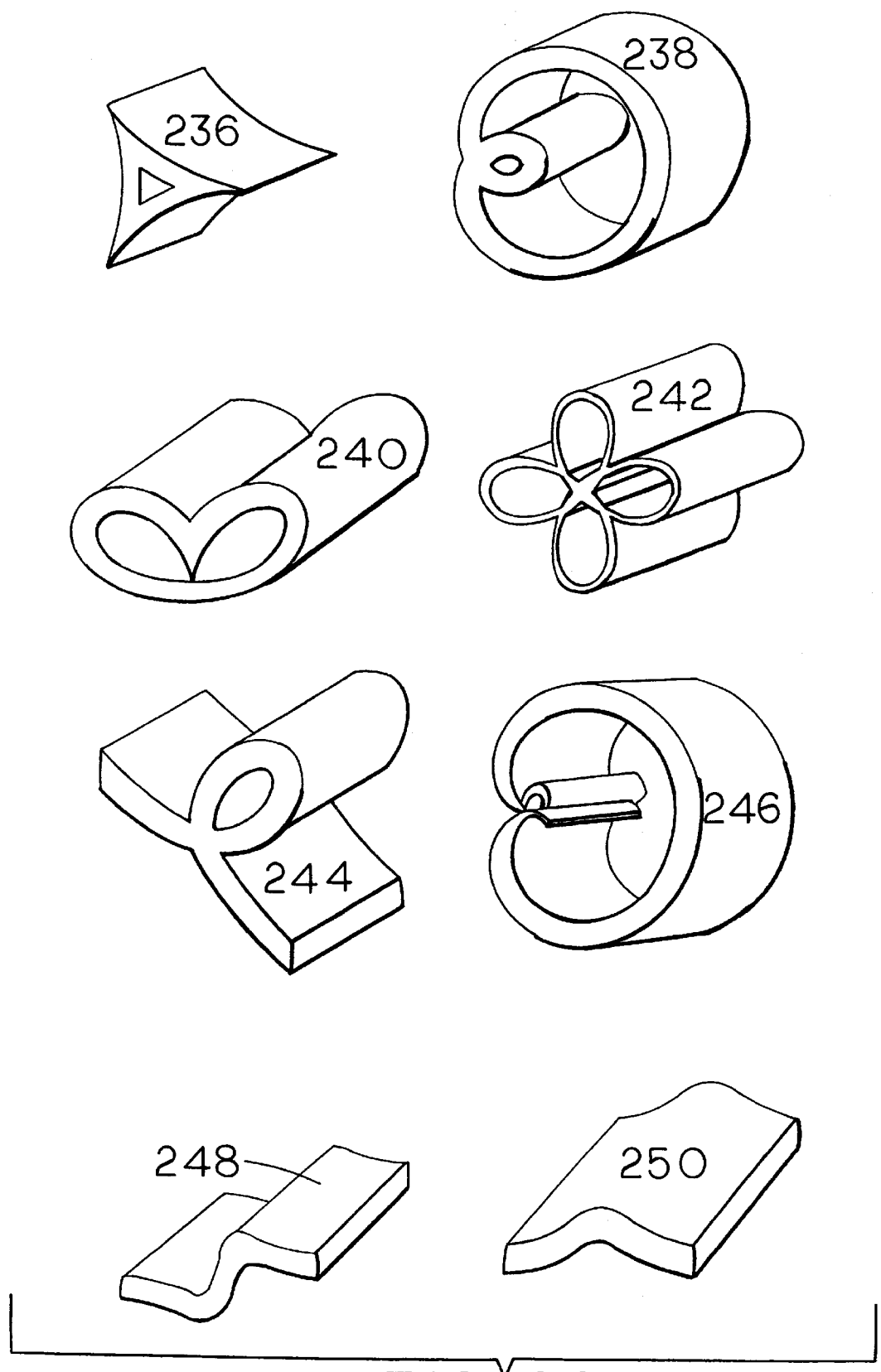
Figure 10E:
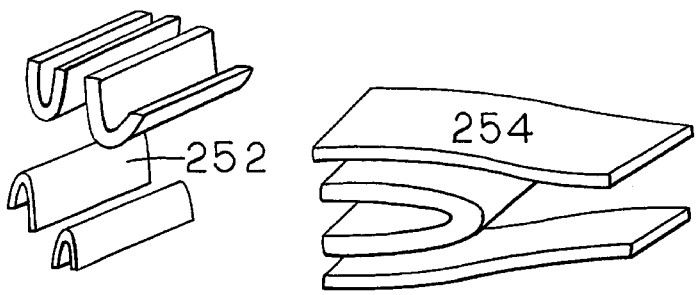

As shown in FIGS. 7(A, B, C), according to another embodiment it may be preferable that the shape of the enclosure is selected from the group consisting of a sphere (138), a hemisphere (140), a zone and segment of one base (142), a zone and segment of two bases (144), a spherical sector (146), a lune (148), a cylinder (150), a cone (152), an elliptic paraboloid (154), a hyperboloid of one sheet (156), a hyperbolic paraboloid (158), an ellipsoid (160), a torus (162), a pyramid (164), a moebius strip (166), a klein bottle (168), a handle (170), a concave polyhedron (172), or a convex polyhedron.

Each of these shapes will have somewhat different sound baffling characteristics. Although the vacuum in the enclosures makes the shapes substantially opaque to sound, sound deflection or sound reflection or sound absorption should still occur. And the sound deflection or sound reflection or sound absorption may be influenced by the shape of the enclosure. The selection of these shapes may therefore influence the characteristics and values of the ambient sound.

Also these devices casts a sound shadow which may be more pronounced than that of previous devices because of the absence of any substantial transmission through the enclosure. This shadow is also influenced by the shape of the enclosure.

Regular polyhedrons may produce a substantially symmetrical sound reflection and sound deflection when used to baffle sound. It may therefore be preferable that the invention comprises an enclosure shaped like a convex polyhedron selected from the group consisting of a tetrahedron (174), a hexahedron (176), an octahedron (178), a dodecahedron (180), or an icosahedron (182). These regular polyhedrons are shown in FIG. 8 which also includes a drawing of the prism (184) and the antiprism (186).

The prism is a polyhedron with two congruent and parallel faces that are joined by a set of parallelograms. The prism is semiregular if all the polygons are regular. Conversely, the antiprism is a polyhedron with two congruent and parallel faces that are joined by a set of triangles. The antiprism is semiregular if all the polygons are regular.

As both the prism and the antiprism may be semiregular, they may give rise to quasi-symmetrical sound deflection or sound reflection when used to supply the shape of an sound baffling device. These symmetries may have an axis depending on the semiregularity of these polyhedra. Hence these shapes may create a sound baffling device with an axial preference. Therefore it may be preferable that the invention is comprised of an enclosure shaped like a convex polyhedron selected from the group consisting of a prism, or an antiprism.

Further polyhedra may be created by stellation or by creating the dual of an existing polyhedron. A stellated polyhedron is formed by extending in the same plane each face of a convex polyhedron until the faces intersect to form a new enclosing shape. For example, the stella octangula is formed by stellating an octahedron. Alternatively, a dual polyhedron is formed by joining a point that is perpendicularly above the centre of each face of a polyhedron to equivalent points above all the neighbouring faces. The cube and the octahedron exemplify dual polyhedra.

The prism and the antiprism have as duals the dipyramids and the trapezohedra, respectively. One would expect that further symmetrical sound baffling advantages may accrue to sound baffling devices shaped after these polyhedra. Accordingly, it may be preferable that the invention comprises an enclosure shaped like a polyhedron created from the aforesaid convex polyhedrons by means of stellation or by creating the duals of said convex polyhedrons.

The enclosures that have been described thus far have the dimensions of solid figures. Although enclosures shaped like solid figures may have many uses, it may often be preferable to fashion the enclosures to substantially resemble a plane or sheet. As shown in FIG. 9 according to one of its aspects the invention comprises an enclosure shaped like a hollow sheet extending in both the x direction and the z direction of the xz plane, the upper (188) and lower (190) surfaces of said sheet having a curvature (192) given by their divergence from the xz plane, such that said curvature may be defined as a function of the y co-ordinate of the xyz co-ordinate system.

These sheets may be shaped to suit the acoustic environment. They may therefore have bumps (193) or hollows (194) as considered useful with regards to some sound baffling or sound deflection or sound reflection or sound absorption applications in mind. These sheets may also be constructed so as to be equidistant from each other as may be found useful for some applications. It may therefore be preferable that the upper and lower surfaces of said hollow sheets are fashioned so as to be substantially equidistant.

The sheets may further have a curvature that fits certain well known mathematical functions. And each of these curvatures may have a unique sound baffling capability. Therefore, as shown in FIGS. 10(A, B, C, D, E) according to another of its aspects the invention comprises an enclosure shaped like a hollow sheet extending in both the x direction and the z direction of the xz plane, the upper and lower surfaces of said sheet being substantially equidistant from each other and having a curvature given by a mathematical relationship defined in the xy plane, said relationship selected from the group consisting of a sinusoid curve, a sine curve (196), an inverse sine curve, a hyperbolic sine curve (198), a cosine curve, an inverse cosine curve, a hyperbolic cosine curve (208), a tangent curve (200), an inverse tangent curve, a hyperbolic tangent curve (202), a secant curve, an inverse secant curve, a hyperbolic secant curve (210), a cosecant curve (204), an inverse cosecant curve, a hyperbolic cosecant curve (206), a cotangent curve, an inverse cotangent curve, a hyperbolic cotangent curve (212), a logarithmic curve (214), a parabola (216), a semicubical parabola (218), a cubical parabola (220), a serpentine curve (248), a trajectory curve, a hyperbola (222), a rectangular hyperbola, an equilateral hyperbola, an ellipse (224), a circle, an evolute of an ellipse (226), an involute of a circle (228), an equiangular spiral (230), a hyperbolic spiral, a parabolic spiral, a spiral of Archimedes, a companion to the cycloid, a cycloid (232), a witch of Agnesi (250), a hypocycloid, a deltoid (236), an astroid, a nephroid, an epicycloid (234), a cochleoid (246), a stropheoid, a conchoid of Nicomedes, a folium of Descartes (244), a bifoleum (240), a lemniscate of Bernouilli, an n-leaved rose (242), an oval of Cassini, a limacon of Pascal (238), a cardioid, a cissoid of Diocles, a lituus, a tractrix (FIG. 13, 290), a power function curve, an exponential curve, a probability curve (FIG. 13, 292), a gamma function curve (252), a quadratic of Hippias (254). Each of these curves may be applied to the sheet, thereby comprising one of the embodiments of the invention. As shown in FIGS. 10(A, B, C, D, E), although the overall effect is three dimensional, when viewed along the length of the z-axis, the sheet describes the selected curve in the xy plane.

Since many of these curves have a very similar visual appearance, a separate drawing was not provided for each of them. For example, the sinusoid curve, having an equation of $y=a(\sin(bx-c))$, has a very similar appearance to the sine curve (196) with equation $y=\sin x$. The cosine curve is also shaped just like the sine curve but with equation $y=\cos x$ will intersect the y-axis where $y=1$ instead of where $y=0$. It may also have a shape modified by constants like the sinusoid. And the other trigonometric functions may have modified shapes derived in a similar fashion.

When the co-ordinate system is not applied the sine and cosine curves are indistinguishable. The same can be said for the secant and cosecant (204) functions. And this may also be said for enclosures having a shape taken from the inverse trigonometric functions. These shapes are the same as the shapes taken from the regular trigonometric functions. The only noticeable difference may be a ninety degree rotation when a co-ordinate system is applied.

Tangent (200) and co-tangent functions differ to a greater degree. Although the shapes are identical, they should differ by a rotation of 180' and when the co-ordinate system is applied should also be offset from each other by a value of pi/2 from the origin. (Pi is throughout this exposition used to represent the transcendental number 3.24159 . . . . )

Enclosures taking their shape from the hyperbolic functions all use equations based on the natural logarithmic base e. For sinh (198) we have; $\sinh x=(e^x-e^{-x})/2$. The other hyperbolic functions have similar equations which are well known.

Logarithmic (214) curves have the equation; $y=\log_a x$. A parabola (216), semicubical parabola (218), and a cubical parabola (220) have the equations, $y=x^2$, $y=x^{2/3}$, and $y=x^3$ respectively. A trajectory is also a parabola having the equation $y=x\tan@-gx^2/(2v^2\cos^2@)$ (@ is used to symbolize an angular measure for the duration of this exposition). The equation for the hyperbola (222) is also well known as $x^2/a^2-y^2/b^2=1$. For the equilateral hyperbola the equation is taken to be $x^2-y^2=a^2$ while the equation of the rectangular hyperbola is taken to be $xy=k$.

The equation for the ellipse (224) is also well known as $x^2/a^2+y^2/b^2=1$, and where $r=a=b$, gives the equation of the circle as $x^2+y^2=r^2$. The evolute of the ellipse (226) is more complicated. Here the equation is $(ax)^{2/3}+(by)^{2/3}=(a^2-b^2)^{2/3}$.

The co-ordinates for the locus of points on the involute of a circle (228) are given by $x=a\cos@+a@\sin@$ and $y=a\sin@-a@\cos@$. The shape of this locus is very similar to the shape of a spiral. An equiangular spiral (230) is shown in the drawings, having the equation $\log r=a@$. The spirals may also be hyperbolic, parabolic, or the spiral of Archimedes, with equations $r@=a$, $(r-a)^2=4ak@$, $r=a@$, respectively.

The witch of Agnesi (250) has an equation of $y=a^3/(x^2+a^2)$. The companion to the cycloid is a form of sinusoid having x and y co-ordinates given by $x=a@$ and $y=a(1-\cos@)$. The locus of the cycloid (232) with the cusp at the origin is given by $x=a(1-\sin@)$ and $y=a(1-\cos@)$. Although these equations maintain the same general form they vary depending on whether the cycloid has the vertex at the origin or is curtate or prolate. The deltoid (236) is a hypocycloid of three cusps whereas the astroid is a hypocycloid of four cusps. The locus of the deltoid is given by $x=2a\cos@+a\cos2@$, $y=2a\sin@-a\sin2@$ whereas the locus of the astroid is given by $x=a\cos^3@$, $y=a\sin^3@$. A nephroid is an epicycloid of two cusps whose locus is defined by $x=a(3\cos@-\cos3@)/2$, $y=a(3\sin@-\sin3@)/2$. The general co-ordinates for the locus of an epicycloid (234) are given by $x=(a+b)\cos@-b\cos((a+b)@/b)$, and $y=(a+b)\sin@-b\sin((a+b)@/b)$. A cardioid may be defined by the equation $r=a(\cos@+1)$ or $r=a(\cos@-1)$. A cochleoid (246) follows the equation $r@=a\sin@$.

A stropheoid, a conchoid of Nicomedes, and a folium of Descartes (244) are all curves having a very similar shape. Their equations are given by $r=a\cos2@\sec@$, $(y-a)^2(x^2+y^2)=b^2y^2$, and $x^3+y^3-3axy=0$, respectively. It should be noted that the shape of the conchoid is only similar to the shape of the folium of Descartes for values of $a<b$. If $a>b$ then the shape of the conchoid acquires similarity to the shape of a witch.

A bifoleum is similar to the lemniscate of Bernouilli although it has an equation of $r=a\sin@\cos^2@$. A lemniscate of Bernouilli is a two leaved rose having an equation of $r^2=a^2\cos2@$. This is a special case of the n leaved roses. The roses (242) may have the equations $r=a\cos n@$ or $r^2=a\cos n@$. In the equations sine may be substituted for cosine. This should cause the curves of these two equations to be offset by forty five degrees when a co-ordinate system is applied.

The ovals of Cassini are shaped somewhat like a rose for $b<k$. In actuality they represent a section of a torus and have the equation $(x^2+y^2+b^2)^2-4b^2x^2=k^4$. The limacon of Pascal (238) and the cardioid are also similarly shaped having equations $r=b+a\cos@$ and $(x^2+y^2-ax)^2=a^2(x^2+y^2)$, respectively. The cissoid of Diocles is shaped similarly to the shape of the tractrix and has an equation of $r=a\sin@\tan@$. The lituus has a strong resemblance to a spiral except that the tail of the spiral exhibits a reverse curvature. The equation for the lituus is $r^2@=a^2$.

The power function curve having equation $y=x^n$ and the exponential function having equation $y=e^{ax}$ have a shape similar to the hyperbolic and logarithmic functions respectively. The gamma function (252) and the Quadratic of Hippias (254) are two unique multiple curve functions. Their equations are given by $T(n)=$(Integral from zero to infinity) $x^{n-1}e^{-x}dx$ and $y=x\tan(pi y/2)$, respectively.

When these equations are used to determine a curvature for the enclosure the resultant appearance of the enclosure is a curved sheet which effectively follows a straight line in the z direction. However, it may sometimes be desirable to have a curvature in the z direction as well, thereby combining two curvatures. Essentially this involves combining the y co-ordinate of the above described curves defined in the xy plane with the y co-ordinate of a further curve selected from the same set of above described curves, but further defined in the yz plane. The combining of the two y co-ordinates may be by subtraction, addition, or by taking the average of the two y co-ordinates. Or it could involve any other method of generating a consistent combination.

A result of the combining process may be the creation of two or more y co-ordinates where previously one of the curves had only a one one and onto mapping. For example, combining an ellipse with a parabola should generate this type of outcome. Accordingly, a further embodiment of the invention may be as shown in FIG. 11 according to which the enclosure has a further curvature given by a mathematical relationship defined in the yz plane, said relationship selected from the group consisting of a sinusoid curve, a sine curve (196), an inverse sine curve, a hyperbolic sine curve (198), a cosine curve, an inverse cosine curve, a hyperbolic cosine curve (208), a tangent curve (200), an inverse tangent curve, a hyperbolic tangent curve (202), a secant curve, an inverse secant curve, a hyperbolic secant curve (210), a cosecant curve (204), an inverse cosecant curve, a hyperbolic cosecant curve (206), a cotangent curve, an inverse cotangent curve, a hyperbolic cotangent curve (212), a logarithmic curve (214), a parabola (216), a semicubical parabola (218), a cubical parabola (220), a serpentine curve (248), a trajectory curve, a hyperbola (222), a rectangular hyperbola, an equilateral hyperbola, an ellipse (224), a circle, an evolute of an ellipse (226), an involute of a circle (228), an equiangular spiral (230), a hyperbolic spiral, a parabolic spiral, a spiral of Archimedes, a companion to the cycloid, a cycloid (232), a witch of Agnesi (250), a hypocycloid, a deltoid (236), an astroid, a nephroid, an epicycloid (234), a cochleoid (246), a stropheoid, a conchoid of Nicomedes, a folium of Descartes (244), a bifoleum (240), a lemniscate of Bernouilli, an n-leaved rose (242), an oval of Cassini, a limacon of Pascal (238), a cardioid, a cissoid of Diocles, a lituus, a tractrix (FIG. 13, 290), a power function curve, an exponential curve, a probability curve (FIG. 13, 292), a gamma function curve (252), a quadratic of Hippias (254), and;

said curvature combined with the curvature defined in the xy-plane by taking the y co-ordinate of said mathematical relationship defined in the xy-plane and combining it with the y co-ordinate of said mathematical relationship defined in the yz-plane, so that the resulting y co-ordinates are the y co-ordinates of the curvature of said enclosure in the xyz co-ordinate system.

The advantage which may be conferred by this embodiment is inherent in the usefulness which may be gained from having a wide variety of surfaces with predictable sound baffling, sound deflection, sound reflection, or sound absorption characteristics at hand. The greater the variety of such surfaces available the greater the flexibility and the more precise the focus of any practical sound baffling arrangement.

Figure 11:
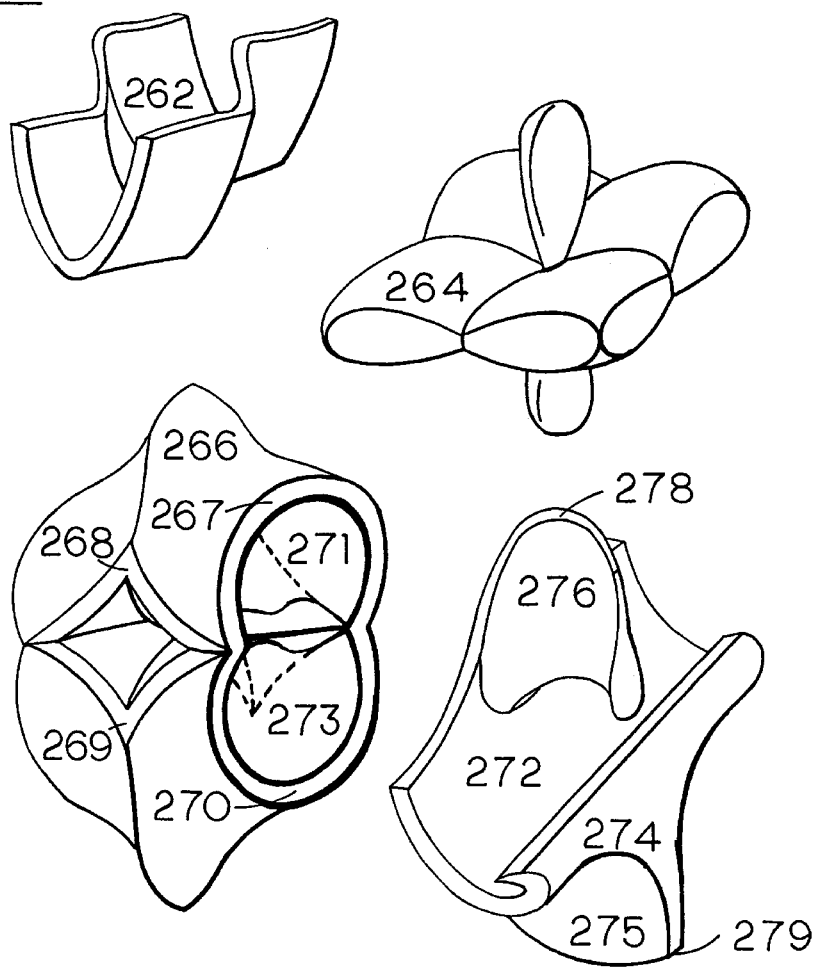
FIG. 11 shows some of the group of enclosures shaped with a three dimensional curvature corresponding to curves defined in the xy plane combined with curves defined in the yz plane.

The enclosures shown in FIG. 11 exemplify this. The first (262) shows a parabola combined with a serpentine curve. The method of combination used here is addition. The y co-ordinates of the two curves are added together giving the resultant set of y co-ordinates. The acoustic characteristics of the resultant enclosures should be substantially different from the acoustic characteristics of the enclosures defined by the curvatures of either the parabola or the serpentine curve when applied in the embodiment defined by a curvature in the xy-plane. (The y co-ordinates are determined in all cases as follows. A $y_f$ and a $y_g$ co-ordinate are derived from each ordered pair of x and z, such that both $f(x, z)=y_f$ and $g(x, z)=y_g$ are defined. The functions are assumed to have a normal position within the co-ordinate system, so that no translation or rotation of the functions is involved unless specified by the rules of combination. Essentially this means that the footprint in the xz plane consisting of all the ordered pairs of x and z, such that for any of these ordered pairs both $f(x, z)$ and $g(x, z)$ are defined, is the basis for selecting the $y_f$ and $y_g$. For any ordered pair $(x_1, z_1)$, all the $y_f$ and $y_g$ corresponding to $f(x_1, z_1)$ and $g(x_1, z_1)$ are selected and combined according to the rules of combination that are in effect. The resulting y combined then function as the new y co-ordinates of the new enclosure which corresponds to the above determined footprint.)

The second enclosure (264) is derived from the combination of two four leaved roses. The equation defining the roses in the xy-plane is the same as the equation defining the roses in the yz-plane, with the exception that the latter equation has z substituted for x in the former equation. The method of combination is by taking the average of the two y co-ordinates. The resulting enclosure no longer strictly fits the category of enclosures formed like a sheet, but rather may be described by the volumetric shape shown in the drawing. And the acoustic characteristics of this enclosure should differ somewhat from the acoustic characteristics of either of the defining roses, as exhibited when they are applied to generate an enclosure in accordance with the embodiment defined by a curvature in the xy-plane.

A further enclosure (266) exhibits a rather convoluted shape. It is derived from the intersection of two tunnel like enclosures fashioned after the curvature of the Nephroid as defined in the xy-plane and the curvature of the astroid as defined in the yz-plane. The method of combination is by subtraction. The footprint y co-ordinates of the Nephroid are subtracted from the footprint y co-ordinates of the astroid. The origin of the co-ordinate system should be substantially near the centre of the node of intersection which is shown in the drawing. This takes cognizance of the fact that both f(x, z) and g(x, z) must be defined. To extend the operation into a region where one or the other of the curvatures is not present, would not be a true combination but merely an operation on one or another of the enclosures as though taken separately. Non-relevant elements are therefore excluded.

As can be seen, this method of combination actually creates internal walls within the node. This is due to the fact that either curve, excepting extremities, in general has two y co-ordinates for every x or z co-ordinate. Therefore subtracting the first $y_f$ from the first $y_g$ gives the first y combined. Subtracting the second $y_f$ from the first $y_g$ gives the second y combined. By applying the same procedure, two more y combined may be obtained from the second $y_g$. This results in a total of four y combined values which function as co-ordinates for the enclosure. As shown in the drawing, four walls (267, 268, 269, 270) cross the node, one for each y combined. And two false interior walls (271, 273) extend into the enclosure from walls (267, 270), creating two hidden enclosures within the enclosure. As before, the unique shape of this enclosure should give rise to a unique set of acoustic characteristics.

Lastly we have the enclosure (272) produced by combining an involute of a circle with a folium of Descartes by means of division. The folium of Descartes is defined in the yz plane whereas the involute is defined in the xy plane. And additionally the folium is rotated by forty-five degrees so that the loop of the folium may be bisected by the y-axis. The $y_f$ of the involute are then divided by the appropriate $y_g$ of the folium. This should produce the y combined of the enclosure shown in the drawing.

Because the arms of the folium are directed away from the head of the folium, when the cusp of the folium is centred on the origin the y co-ordinates of the arms are negative whereas the y co-ordinates of the head are positive. Division of the involute by the $y_g$ of the folium will therefore tend to invert the curvature of the involute whereas division by the y co-ordinates of the head will tend to accentuate it. This results in the boat like appearance of the enclosure shown in the drawing. The hull (274) of the boat shape is derived from the arms of the folium whereas the sail (276) and cabin (277) are derived from the head of the folium. The keel (275) of the boat shaped combination is derived from the region where the arms curve inward toward the origin.

Mathematically, the top (278) of the sail shape should asymptote upward to infinity, as should the bottom (279) of the keel. In practice, as shown in the drawing, an upper and lower bound are chosen to establish the limits necessary for the creation of a functioning enclosure. These values are chosen so as to be most applicable for the particular use for which the enclosure is created. As one might deduce from its shape, this enclosure should also have acoustic characteristics that are substantially different from the acoustic characteristics of the enclosures which may be based on the defining curvatures when applied in the embodiment defined by a curvature in the xy-plane.

It is clear from the preceding discussion that the enclosures of the embodiment using two curvatures defined in the xy-plane and the yz-plane respectively, may amount to a very large number. This is because they are defined both by the curvatures used and by the methods and conventions whereby they are combined. For brevities sake, the description of the enclosures using two defining curvatures will be limited to the ones so far discussed. Additionally it should be noted that certain pragmatic steps may be needed in the construction of a functioning enclosure. These may include the truncation of non-relevant elements of the combination and the setting of upper or lower bounds on asymptotic extensions of the extremities. Unwelcome cavities resulting from the combination may also be closed off or opened up by adding or removing walls, and the locus of the functions may be restricted so that only certain values of $y_f$ and $y_g$ are produced. It should further be noted that the drawings supplied in FIG. 11 are descriptive in nature and should not be relied upon to furnish data.

Figure 12:
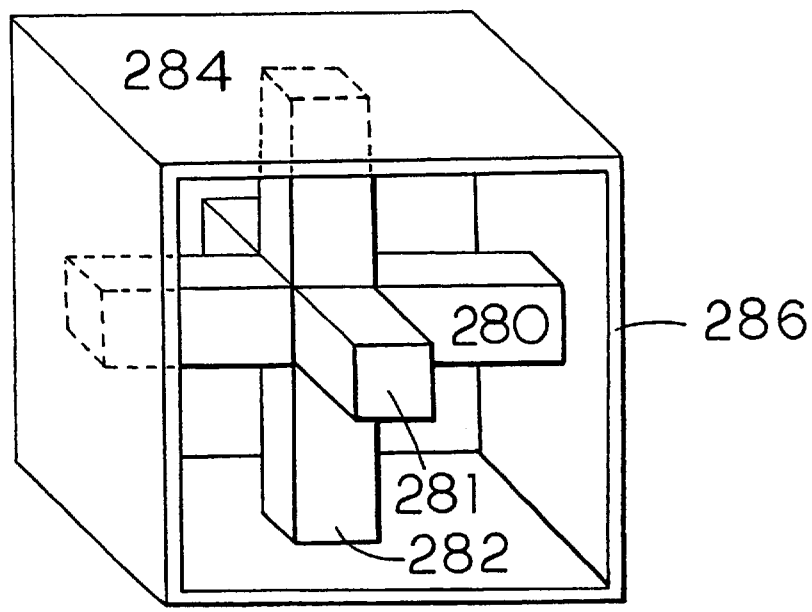
FIG. 12 is a sectional drawing illustrating the supporting struts that may be used within an enclosure for counteracting the external pressure.

Depending on the size and width of the enclosure and the material used in its construction as well as the external pressure present at the surface, structural instability may result. This could result in total collapse of the enclosure or more simply just the touching of the two sheets that form the surfaces of a planar enclosure. When such touching occurs sound may be transmitted through the enclosure where the sheets touch, thereby reducing the effectiveness of the enclosure. This may be counteracted by placing appropriately constructed struts within the enclosure in accordance with the principles of structural engineering. Therefore, as shown by the cross-sectional drawing of FIG. 12, according to one of its aspects the invention comprises an enclosure having a plurality of supporting struts (280, 281, 282) for counteracting external pressure present at the surface (284) of said enclosure, said supporting struts placed and attached between the walls (286) of said enclosure, so that the structural integrity of said enclosure is maintained. The material for these struts should also be selected to minimize the transmission of sound so as to maintain the enclosure at the maximum opacity to sound. When the enclosure is comprised of essentially equidistant sheets, the struts may be better described as dividers or spacers. Equidistant sheets comprising an enclosure are most vulnerable to external pressure and, if spacers are to be avoided, strong materials should be used. The regular convex polyhedrons and their close companions, the sphere, cylinder etc., are least vulnerable to external pressure as they display a certain surface stability due to their geometry. The surfaces reinforce each other.

All of the preceding embodiments should function well when applied to baffle sound. However, in application they are static because they provide a constant amount and quality of sound baffling. It may therefore be preferable that the invention also have the capability to vary the amount and quality of the sound baffling provided. The key idea here is that because the presence of the vacuum within the enclosure should make the device essentially opaque to sound transmission, when matter is admitted to the enclosure sound transmission through the enclosure is enabled. The amount of the sound transmission should then be proportional to the amount of matter that is admitted. And the converse procedure applies as well. This is illustrated in one part of FIG. 13 according to which the invention further comprises a means for admitting and removing matter (288) connected to said enclosures (290, 292) by means of valves (294, 296), so that by admitting and removing matter to and from said enclosures the sound baffling characteristics of said sound baffling device are varied by said admitting and said removing.

The means for admitting and removing may use some type of vacuum pump to remove the matter from the enclosures. The vacuum pump may be motor driven or operated manually in some applications. After the matter has been removed from the enclosures, it can be readmitted by using the external pressure as a driving force. All that is required is a two way valve. Such a valve could be used, in either manual or automatic operation, for either the admitting or removing of matter from the enclosures.

Accordingly, this embodiment exhibits the ability to baffle sound in a dynamic fashion. While this may have been done previously by rotating or moving the enclosures, the invention shows how the admitting and removing of matter to and from an enclosure may be used to baffle sound dynamically. In general admitting matter to the enclosure should decrease the sound baffling characteristics of the enclosure and removing matter from the enclosure should increase the sound baffling characteristics of the enclosure. It may therefore be preferable that said admitting increases the transmission of sound through the enclosures and said removing decreases the transmission of sound through the enclosures.

Most applications involving dynamic sound baffling will probably require more than one enclosure to effectively adjust the ambient sound. This follows from the fact that for many applications, such as the adjustment of acoustics in a theatre or lecture halls, the ambient acoustic environment is frequently changing. For example, the entry and exit of people to and from a lecture hall should change the values and characteristics of the ambient sound. A dynamic adjustment of the sound baffling characteristics of the sound baffling device is therefore required to maintain the acoustic characteristics close to optimum.

This dynamic adjustment of a sound baffling device is best handled by a controlling means. Accordingly, the preferred embodiment of the invention which is designed to handle complex applications is illustrated in the greater part of FIG. 13, according to which the invention further comprises a controlling means (298), said controlling means having an input means (300) for entering and storing parametric values (302), and;

said controlling means further having a means for measuring (304) the values and characteristics of the ambient sound, said means for measuring having sensor inputs (306, 307) placed throughout the extent of the physical space (308) which is governed by said sound baffling device, and;

said controlling means further having a means for correlating (310) said measured values and characteristics (312) of the ambient sound to said stored parametric values, and;

said means for correlating using the correlation (314) between said measured values and characteristics of the ambient sound and said stored parametric values as a benchmark for adjusting said means for admitting and removing of matter, such that matter is admitted and removed from said enclosures as indicated by said benchmark, so that the measured values and characteristics of the ambient sound throughout the physical space which is governed by said sound baffling device enter a convergence towards said stored parametric values, and;

after a requisite interval of time an optimum correlation between said stored parametric values and said measured values of the ambient sound is attained.

The underlying objective of the preferred embodiment is to allow the user of the sound baffling device to choose the values and characteristics of the ambient sound to a degree closely corresponding to the users preferred values and characteristics for the ambient sound. The user may accomplish this by entering the preferred values and characteristics as the parametric values and characteristics of the ambient sound (302) into the input means (300). These values and characteristics may be any parameter that has been used or may be used to characterize the sound. However, the input means of some preferred embodiment may not accept the universal historical set of potential parametric values and characteristics. In such a case the parametric values and characteristics of the ambient sound accepted by the input means will be a subset of the universal parametric set of values and characteristics of sound.

Values and characteristics that may in general be accepted as parameters by the input means are, loudness, reverberation, and timbre. Further values and characteristics that may be settable are, pitch, attack, and decay. After the settable values have been entered they are compared to the measured values and characteristics (312) gathered through the means for measuring (304) which has sensor inputs (306, 307) that measure the values and characteristics of the ambient sound throughout the physical space (308) governed by the sound baffling device. The comparison itself is carried out by the means for correlating (310) which should adjust the sound baffling device through the means for admitting and removing if it finds that the difference between the measured values and characteristics and the selected parametric values and characteristics is sufficiently large as to require adjustment. The adjustment should then create values and characteristics for the ambient sound that correspond more closely to the selected parametric values and characteristics of the ambient sound stored in the input means.

The technology used to implement the controlling means (298) may be based around a microprocessor governed by a controlling program designed specifically for this task. While optional, the controlling program and microprocessor effectively should augment the means for correlating while the other means may be implemented by dedicated hardware. The input means may simply be some kind of data entry console as exemplified by a PC terminal and keyboard. Or it may be a set of switches in conjunction with LED readouts or dials, as may be deemed most appropriate for a particular design. The means for measuring should have sensors (332, 333) for testing the ambient sound, the most obvious of which would of course be microphones placed strategically throughout the physical space which is governed by the sound baffling device. The information from these sensors may then be converted into a digital representation useable by the means for correlating in carrying out the comparison of the values and characteristics of the ambient sound. And this digital representation should also be useable by the controlling program and the microprocessor (334).

The controlling program should contain an acoustic model of the physical space under consideration. This model is derived from, and constructed in accordance with the principles of acoustic science and includes the effects of the placement and shape of the enclosures (290, 292) on the values and characteristics of the ambient sound. And this model is also capable of estimating the effects of various amounts of matter present within the enclosures on the ambient sound. By using this model and the input parametric values and characteristics as a basis for the initiation of calculations, the controlling program should be able to estimate the appropriate level of matter which should be present within each of the enclosures. Subsequent to the calculation of this estimate, the controlling program and the microprocessor should then generate the necessary set of instructions for the means for admitting and removing.

The means for admitting and removing should have a sealed piping network (335, 336, 338, 340, 342) to enable the admitting and removing of matter to and from the enclosures. The piping network may have a separate valve (294, 296) for each pipe leading from the means for admitting and removing to each enclosure. The means for admitting and removing should also have controlling lines (344, 346, 348, 350, 352) for setting the valves as well as a vacuum pump connected to the pipes by means of the valves. Upon receiving the appropriate instructions the valve leading to an enclosure where matter is to be admitted and removed is opened or closed to a degree determined by the instructions. Then matter is removed through the action of the vacuum pump if required. Or matter may be admitted by means of the external pressure, if that is what is required. The external pressure may force air into the enclosures directly through an intake valve contained in the means for admitting and removing. This intake valve may also function as an exhaust valve for the vacuum pump. The means for admitting and removing may therefore also contain an apparatus for enabling either the vacuum pump or the external pressure to act on the piping network by means of this intake or exhaust valve. Alternatively, the matter may be retained within the means for admitting and removing. This implies that a storage chamber for storing matter is contained within the means for admitting and removing. The storage chamber is capable of storing all the matter that is present within the enclosures, the piping network, the vacuum chamber, and the vacuum pump. Matter may therefore be removed from the enclosures and stored in the storage chamber by the means for admitting and removing. Or some of the same matter may be admitted to the enclosures by the means for admitting and removing. The implementation of either admitting or removing is carried out on the basis of information received from the means for measuring.

If the measured values and characteristics of the ambient sound do not have a sufficiently close correspondence to the input parametric values and characteristics of the ambient sound then matter is either admitted or removed to increase this correspondence. Then, after the admitting or removing of matter has been carried out by the means for admitting and removing, new measurements of the values and characteristics of the ambient sound in the physical space controlled by said sound baffling device are taken. These new measured values and characteristics of the ambient sound are then correlated by the means for correlating to the stored parametric values and characteristics of the ambient sound and, if the new correspondence lies within a parametrically set degree of accuracy, the procedure of adjusting the sound baffling characteristics of the sound baffling device is halted.

Alternatively, if the new measured values and characteristics of the ambient sound do not have a sufficiently close correspondence to the stored parametric values of the ambient sound, the procedure is repeated. The controlling means therefore has a feedback mechanism implemented by the means for correlating which carries out adjustments based on the measured values and characteristics of the ambient sound until the parametric values and characteristics of the ambient sound and the measured values and characteristics of the ambient sound agree within a parametric level of accuracy set by the input means. When such agreement is reached the means for correlating enters a sampling loop that checks periodically to ensure that the agreement of the values and characteristics of the ambient sound continues. Should the agreement be lost the adjustment of the sound baffling characteristics of the sound baffling device should resume.

The controlling program may carry out the actual correlation and determination of values. Basically three sets of variables may be used as well as one set of constants or operating principles. The first set of variables is just the set of parametric values and characteristics (302) of the ambient sound input by the operator or user of the sound baffling device. The second set of variables, which may also be input by the user, simply lists the tolerances required for each of the values and characteristics of the ambient sound before the convergence procedure carried out by the controlling means may be terminated. The last set of variables lists the actual measured values and characteristics (312) of the ambient sound as of the last reading of the sensors.

The means for correlating will have default settings for the first and second set of variables. This may ensure that, if the controlling means is engaged and no parametric values and characteristics of the ambient sound are entered through the input means, the sound baffling device will still function in a useful way. When a controlling program is used, the set of constants and operating principles contained within the controlling program should act on the data received by the sensors with reference to the default values of the means for correlating.

These constants and operating principles are essentially drawn from the science of acoustics. The spatial configuration of the sound baffling device is evaluated scientifically and the relevant data is entered into the controlling program as a list of constants. Specifically the data comprises a description of the physical space to be controlled, the number of enclosures used, and the shape, disposition and size of the enclosures as well as the interaction among these entities.

The operating principles are drawn from the science of acoustics and are stored in the controlling program. They are comprised of the equations of acoustics as well as algorithms using these equations to calculate and predict an acoustic result. In the application of these equations and algorithms, the constants drawn from the specific case data are substituted by the controlling program for the appropriate variables in the equations and algorithms. The equations and algorithms may then be used to predict the values and characteristics of the ambient sound in the controlled physical space for a given state of the sound baffling device.

The controlling program then compares the predicted values and characteristics of the ambient sound with the parametric values and characteristics of the ambient sound read into the program from the input means. By means of the equations and algorithms the controlling program then estimates the change in the state of the sound baffling device required to create the parametric values and characteristics of the ambient sound within the physical space governed by the sound baffling device. Having estimated the necessary change, the controlling program then sends a requisite list of instructions through the means for correlating to the means for admitting and removing which, by admitting or removing matter in the required amounts to and from the various enclosures changes the state of the sound baffling device.

The controlling program then checks the measured values and characteristics of the ambient sound to see if they now lie within the allowed parametric tolerance. If the measured values and characteristics of the ambient sound lie within the parametric tolerance, the controlling program next enters a sampling loop. In the loop it samples the measured values and characteristics of the ambient sound and the input parametric values and characteristics of the ambient sound at a preset parametric rate. If a difference between the measured values and characteristics of the ambient sound and the parametric values and characteristics of the ambient sound falling outside the parametric tolerance is found by sampling, then a new set of instructions is sent to the means for admitting and removing, so that this difference may be reduced to fall within the parametric tolerance. In this fashion the controlling means converges automatically to establish an optimum correlation to the preferred set of parametric values and characteristics of the ambient sound in the physical space governed by the sound baffling device. But the optimum correlation may not be a total correlation. Rather the optimum correlation should be the best correlation attainable with the input values and characteristics of the ambient sound when used in combination with the physical structure of a particular embodiment and the physical space it governs. And this correlation may, in certain instances, not be discernible by the controlling means. For instance, this would occur where subsequent to the operation of the controlling means for an arbitrary period of time, all of the preferred set of parametric values and characteristics still had not found a match lying within the parametric tolerance, to any of the elements of the set of measured values and characteristics. Therefore, if after a preset number of trials, one or more of the preferred set of parametric values and characteristics still have not found a match within the parametric tolerance to the corresponding set of measured values and characteristics, the convergence procedure may, at least temporarily, be aborted with respect to the offending parametric values and characteristics. This may be done by simply removing the parametric values and characteristics in question for a determined number of iterations from the total list of values and characteristics which must be considered by the controlling means. Alternatively, the parametric tolerance may be increased.

For embodiments that function without the optional controlling program and microprocessor, some tasks normally handled by these elements may be assumed by the operator. And the controlling means may also have additional on board hardware for dealing with some of these tasks. This may involve the use of additional circuitry and/or the use of programmable logic devices.

To speed up the removal of matter from the enclosures, it may be found useful to maintain an appropriately sized vacuum chamber in an evacuated state. As shown in a still further part of FIG. 13, the vacuum chamber is also connected to the enclosures through the valves and the piping network. When the valves between the enclosures and the vacuum chamber are opened, the matter rushes from the enclosures into the vacuum chamber, thereby causing the enclosures to be evacuated at a high speed. This allows the matter within the enclosures to be adjusted more rapidly. It may therefore be preferable that the invention further comprises a large vacuum chamber (316) connected by chamber valves (318, 320) to said sound baffling device, said vacuum chamber maintained in a state of vacuum by means of a removal valve (322) and pipe (335) connecting said vacuum chamber to said means for admitting and removing, so that when said controlling means causes said chamber valves to open, pressurized matter present within said enclosures flows rapidly into said vacuum chamber, so that the speed with which the matter within said enclosures is removed is optimized. And, it may also happen that during the design and construction of the preferred embodiment it is found that a certain state of the sound baffling device is preferable. This is to say that during the normal operation of the controlling means, the enclosures of the sound baffling device would for a major part of the operation have a certain preferred amount of rarefied matter within them. It may therefore be preferable that, after creating the preferred state of rarefied matter within the enclosures by the action of the means for admitting and removing, that the means for admitting and removing as well as the controlling means are removed from the enclosures, thereby leaving the enclosures as separate entities having the preferred state of rarefied matter contained within them.

This may also be accomplished by a third process of manufacture that uses a means for the admitting and removing of matter to create a preferred rarefaction of matter within an enclosure, said third process having the following steps in the sequence set forth;

the first step in the third process of manufacture comprising the admitting or removing of matter to or from said enclosure to create said preferred rarefaction of matter within said enclosure, the second step in the third process of manufacture comprising the sealing of said enclosure, such that the rarefied matter within said enclosure is preserved against contact with ambient matter, the third step in the third process of manufacture comprising the removal of said means for admitting and removing from said enclosure, so that an enclosure having a preferred sound attenuation is created upon the completion of said third process of manufacture.

The application of the third process should also allow a reduction in the overall costs of a sound baffling device comprised of a number of enclosures acting in concert, because the cost of the controlling means and of the means for admitting and removing need not be defrayed on a permanent basis. Rather the means for admitting and removing and the controlling means, which may be comprised of manual controls exercised by an operator, should only be used to create the preferred state of rarefied matter. Subsequently they should be removed so that they may be used in the preparation of another sound baffling device. This procedure may therefore be used for enclosures fashioned to suit a situation where total sound reduction is not desired, or alternatively a reduced level of sound transmission is desired. The enclosures may simply be prepared by a suitable means for admitting and removing to have the preferred state of rarefied matter that produces the desired state of sound attenuation. The enclosures are then sealed and the means for admitting and removing is separated from the enclosures. Thus enclosures having a specified amount of sound attenuation may be produced.

Alternatively, to produce a large number of enclosures having a preferred amount of rarefied gas or air within them, a vacuum chamber may be used. This is most applicable to those embodiments of the invention where the enclosures do not permit the admitting or removing of matter. In operation the vacuum chamber is evacuated to produce the desired rarefaction of matter and, after the rarefied matter has been incorporated into the enclosures they are sealed. This procedure may be carried out by means of robotics or it could be performed by appropriately equipped men. Accordingly another aspect of the invention may be given by embodiments selected from the group consisting of enclosures containing a homogeneous means for attenuating sound, or a material having a cellular structure wherein each cell is an enclosure containing a homogeneous means for attenuating sound, or a material having a cellular structure that has been created from a material having a porous structure and wherein each cell is an enclosure containing a homogeneous means for attenuating sound, and;

wherein the construction of said embodiments is carried out within a vacuum chamber, said vacuum chamber evacuated to create a preferred rarefaction of the matter within said vacuum chamber, such that during construction said preferred rarefaction of matter is incorporated into the enclosures of said embodiments to comprise said homogeneous means for attenuating sound, so that in operation said embodiments produce a preferred sound attenuation. And it may further be preferable that for said embodiments the preferred rarefaction of matter within said vacuum chamber corresponds as closely as possible to a perfect vacuum, such that during construction said preferred rarefaction of matter is incorporated into the enclosures of said embodiments to comprise said homogeneous means for attenuating sound, so that in operation said embodiments produce an optimum sound attenuation.

The degree of rarefaction is chosen to establish a preferred attenuation for the transmitted sound. And these procedures may also be used to create a composite cellular material from a suitable product, so that the composite cellular material has a specified sound attenuation. This is done by incorporating a specified amount of rarefied matter into the product suitable for pouring. The composite cellular material is then created by the previously described methods.

However, for those embodiments of the invention where the enclosures do not permit the admitting and removing of matter, the creation of the vacuum inside the enclosures may be most easily done in a vacuum chamber. This process of manufacture may be carried out by means of robotics. Or it could be performed by appropriately equipped men. Accordingly, it is preferable that the step in the process of manufacture which creates said enclosure is carried out within a vacuum chamber, so that the vacuum within said vacuum chamber is incorporated into said enclosure.

It is clear from the information previously disclosed, that the invention is capable of a large number of embodiments. And it may have a correspondingly large number or uses. It may therefore be preferable that the use of said invention may be selected from the group consisting of the use of said sound baffling device to create sound proof walls and ceilings, or the use of said sound baffling device to create bricks or building blocks substantially impervious to sound, or the use of said sound baffling device to sound proof holes and gaps within structures or buildings, or the use of said sound baffling device to create sound proof casings for motors, machinery and industrial equipment, or the use of said sound baffling device to create structural components substantially impervious to sound, or the use of said sound baffling device to create movable dividers and partitions that are substantially impervious to sound, or the use of said sound baffling device to sound proof automobile and vehicular bodies, or the use of said sound baffling device to govern the acoustics of amphitheatres, theatres, lecture halls, classrooms, halls, and corridors, or the use of said sound baffling device in the head phone sets of sound monitoring, communication or entertainment equipment, or the use of said sound baffling device to create directional speakers. Because size should not be a factor influencing the efficiency of the sound baffling device, a relatively small sound proof cabinet or housing may be created for directional speakers or speakers in general. This should insure that the major portion of the sound substantially travels through the opening of the housing, thereby lending increased directionality to the emitted sound.

One noteworthy factor for determining the appropriate use of the invention is that one should have an application in mind. Next the values and characteristics of the physical space to which the application is devoted must be measured, defined and examined in accordance with the principles of acoustic science. Thereafter an optimal embodiment of the invention is chosen for the intended use. The method of choice relies on the science of acoustics. Various embodiments may be considered in conjunction with the physical space and their impact on the values and characteristics of the acoustics of the physical space is evaluated. From these, one having optimum effect is chosen. When the embodiment allows only static sound baffling nothing further is required. However for the embodiments which allow dynamic sound baffling, the required parametric values should also be entered to achieve the desired operation. Otherwise these embodiments will operate by using the on board default parameters.

A vacuum may also be used to improve the sound baffling characteristics of ear protectors and head phone sets. As is well known the ear protectors are used to protect the ears from excessive ambient noise. And a prevalent problem with head phone sets is the interference of ambient noise with the audibility and perceived rendition of the rendered sound. This may be alleviated by introducing an vacuum for baffling the ambient noise. However there are some other sound baffling improvements that may be made to ear protectors and head phone sets as well.

Accordingly, a more specific aspect of the invention is shown in FIGS. 14 and 15 which depicts the invention in combination with a set of ear protectors having two sound baffling cups (354, 356) for fully enclosing the ears between said sound baffling cups and the head and neck during operation, and a fitting means (358) for placing said sound baffling cups against the ears, the improvement comprising;

A cushioned lip contour (360, 362) for complimenting the shape of the head and neck during operation, said cushioned lip contour applied to the lips (364, 366) of said sound baffling cups such that said cushioned lip contour curves the lips of said sound baffling cups laterally (368) (The vocabulary is borrowed from human anatomy. The sound baffling cups and the associated art are assumed to be attached to the human body as they would be during operation. The descriptive words (ie. laterally), are then used to describe the relevant embodiments as though these embodiments were a part of the human body.) away from the head where it touches the jaw bone and the side arch of the skull, and said cushioned lip contour curves the lips of said sound baffling cups medianly (370) towards the head and neck where it touches the human body surface beneath the jaw bone and behind the lower external ear, so that the comfort, fit, and sound baffling qualities of said sound baffling cups are substantially improved by said cushioned lip contour, thereby reducing the ambient noise reaching the ears during operation.

Some previously available devices did not have contours. As shown in FIG. 15, since the head and neck have numerous contours, a contoured device provides a better fit and comfort. Also the exclusion and baffling of sound is to some extent dependent on the ability of the sound baffling cups to seal against the head and neck, because this prevents the sound from entering through gaps where the lips of the sound baffling cups are joined against the head and neck. A cushioned lip contour aids in achieving a proper seal, especially under conditions of stress, where the head and neck are bent or when the sound baffling cups are jarred by external contact.

If we consider the lips of previously available sound baffling cups to lie in a sagittal plane parallel to the side of the head during operation, then the cushioned lip contour diverges from this plane by curving laterally (368) away from the head and neck directly above the jaw bone (372). Beneath the jaw bone and the lower external ear (374) the contour diverges from this plane by curving medianly (370) towards the head and neck. This compensates for the hollow of the human body surface found just beneath where the head and neck and jaw bone join. Then, behind the external ear, the contour moves back towards and into this plane, lying substantially in this plane above the external ear.

As shown in FIGS. 16A and 17, another particular of the invention is in combination with two sound baffling cups (376, 377) for fully enclosing the ears during operation, the improvement comprising;

A fitting means for placing said sound baffling cups against the ears, said fitting means having a complementary contour (378, 379) fastened to the interior of said sound baffling cups, said complementary contour corresponding substantially to the convolutions of the external ear by means of a plurality of flexible cushioning grooves and ridges, and;

said complementary contour having a first ridge (382) for extending into the scaphoid fossa, a second ridge (384) for extending into the triangular fossa, a third ridge (386) for extending into the cymba, a fourth ridge (388) for extending into the cavum concha, said fourth ridge having two tongues, the first tongue (390) for extending into the anterior incisure, the second tongue (392) for extending into the intertragic incisure, and;

said complementary contour having a first groove (394) for cushioning the auricular tubercle, the helix, and the crus of helix, a second groove (396) for cushioning the anthelix, said second groove divided by said second ridge into a superior second groove (398) and an inferior second groove (400) for cushioning the superior and inferior parts of the crura of anthelix respectively, a third groove (401) for cushioning the supertragic tubercle, tragus, antitragus, posterior auricular sulcus, and the lobule, and;

said first groove joined to said third groove by the tip of said first tongue, said first, second, and third grooves joined together at the inferior end of said first ridge, and;

said fitting means further having a latching means (402, 403) for latching onto said sound baffling cups, said latching means pressing and holding the external ear against said complementary contour such that the external ear is substantially sealed against said complementary contour by said latching means, so that the ambient noise reaching the ears during operation is substantially reduced by said sound baffling cups. The complementary contour is more complex than the cushioned lip contour. It does not just change the fit of the sound baffling cups along the circular or elliptical opening of the sound baffling cups, but as shown in FIG. 16A, instead has a plurality of flexible grooves and ridges crafted to complement the shape of the external ear. The contour therefore fits into the grooves and hollows of the external ear, thereby creating greater adhesion and a sealing effect between the sound baffling cups and the external ear.

The usual fitting means may therefore be dispensed with, so that the sound baffling cups may simply be clipped onto the external ear with the latching means. This further improves the comfort of the device, as the elastic or metal latching bands used in some previous devices were cumbersome, sometimes applied insufficient tension, and interfered with the wearing of head gear. Hats and other head gear are easily worn when using the clip-on type of fitting means. The complementary contour further braces the front of the external ear, so that when the latching means, which may be a jointed flexible curved clip, is applied to the back of the external ear, the external ear is wedged snugly in between the latching means and the complementary contour. And the complementary contour may also have a supporting base (380, 381) for further improving the fit and comfort of the device. The supporting base should be attached to the interior of the sound baffling cups and may be a necessity when the complementary contour is made of a flexible material requiring support. This device may therefore also function as an improved set of ear protectors because it dispenses with the previously used type of fitting means.

Another particular of the invention is in combination with a head phone set having speakers (404, 405) and a connecting means (406) for connecting said speakers to a playback unit, the improvement comprising;

A fitting means for placing a pair of sound baffling cups (408, 409) against the ears, said speakers attached to the interior of said sound baffling cups, said sound baffling cups fully enclosing the ears during operation, said fitting means having a sound permeable complementary contour (410, 411) fastened to the interior of said sound baffling cups, said complementary contour corresponding substantially to the convolutions of the external ear by means of a plurality of flexible cushioning grooves and ridges, and;

said complementary contour having a first ridge (414) for extending into the scaphoid fossa, a second ridge (416) for extending into the triangular fossa, a third ridge (418) for extending into the cymba, a fourth ridge (420) for extending into the cavum concha, said fourth ridge having two tongues, the first tongue (422) for extending into the anterior incisure, the second tongue (424) for extending into the intertragic incisure, and;

said fourth ridge further having an opening (426) enclosed in its centre, the size and location of said opening corresponding substantially to the size and location of the ear canal, and;

said complementary contour having a first groove (428) for cushioning the auricular tubercle, the helix, and the crus of helix, a second groove (430) for cushioning the anthelix, said second groove divided by said first ridge into a superior second groove (432) and an inferior second groove (434) for cushioning the superior and inferior parts of the crura of anthelix respectively, a third groove (435) for cushioning the supertragic tubercle, tragus, antitragus, posterior auricular sulcus, and the lobule, and;

said first groove joined to said third groove by the tip of said first tongue, said first, second, and third grooves joined together at the inferior end of said first ridge, said fitting means further having a latching means (436, 437) for latching onto said sound baffling cups, said latching means pressing and holding the external ear against said complementary contour such that the external ear is substantially sealed against said complementary contour by said latching means, so that the ambient noise reaching the ears during operation is substantially reduced, thereby improving the audibility and perceived rendition of the sound emanating from said speakers.

Figure 18:
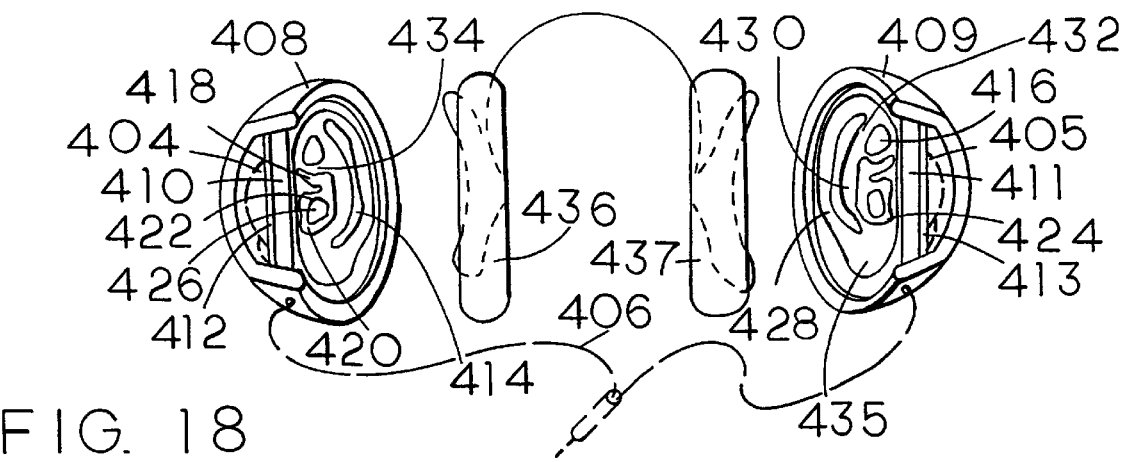
FIG. 18 shows how the latching means and the complementary contours that should be used for head phone sets combine with sound baffling cups and some of the previously known art.

As shown in FIGS. 16B and 18, the complementary contour used for head phone sets is very similar to the complementary contour used for ear protectors in that it is shaped to substantially fit and adhere to the entire external ear. It does this by means of the plurality of crafted cushioning grooves and ridges which complement the shape of the external ear. When a good fit is obtained, these grooves and ridges may elastically adhere to the external ear after being pressed against it, and this elastic tension may contribute to holding the complementary contour against the external ear. However, for head phone sets, the ridge extending into the cavum concha may also have an opening (426) in its centre. In general this opening should be located above the cavum concha and the ear canal. This is to minimize any interference with the sound as it travels from the speakers to the internal ear. The interference may further be minimized by making the complementary contour for head phone sets out of a material that is permeable to sound. And the complementary contour also provides a backing for the latching means, which may be a jointed flexible curved clip, so that when the latching means is applied to the back of the ear lobe, the external ear finds a ready cushion when it is pressed against the complementary contour. Because the complementary contour may contribute to the attachment of the sound baffling cups, the pressure exerted by the latching means may not need to be as strong as it may be for some of the other embodiments. And the complementary contour may also have a sound permeable supporting base (412, 413) for further improving the fit and comfort of the device. The supporting base should be attached to the interior of the sound baffling cups and may be a necessity when the complementary contour is made of a flexible material requiring support.

This embodiment may also enjoy the advantage of better sound baffling characteristics due to the sound sealing characteristics of the complementary contour. Also the usual semicircular fitting means is dispensed with. This contributes to a better overall fit and also allows head gear to be worn.

The complementary contours may be custom made by using a mould made from castings of the external ear. It may therefore be preferable that the complementary contour of said fitting means is created by a mould made from castings of a specific external ear, so that the complementary contour of said fitting means is customized to fit said specific external ear. Such a mould may be made from standard casting techniques and can then be used to create complimentary contours for customized head phone sets and ear protectors.

Figure 19:
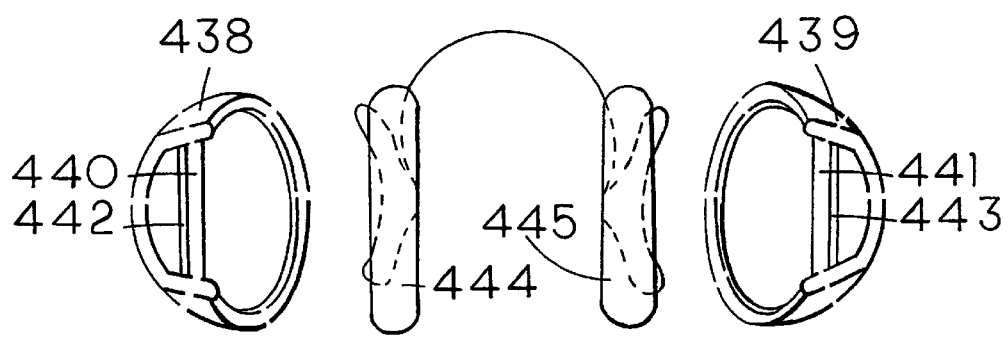
FIG. 19 shows how the latching means and the cushioning material that should be used for ear protectors combines with the sound baffling cups of previously known ear protectors.

As shown in FIG. 19, another particular of the invention is in combination with two sound baffling cups (438, 439) for fully enclosing the ears between said sound baffling cups and the head and neck during operation, the improvement comprising;

A fitting means for placing said sound baffling cups against the ears, said fitting means having a cushioning material (440, 441) fastened to the interior of said sound baffling cups, such that said cushioning material complements the shape of the external ear when said external ear is pressed against it, and;

said fitting means further having a latching means (444, 445) for latching onto said sound baffling cups, said latching means pressing and holding the external ear against said cushioning material such that the external ear is substantially sealed against said cushioning material by said latching means, so that the ambient noise reaching the ears during operation is substantially reduced by said sound baffling cups.

The cushioning material is different from the complementary contour since although it is shaped to fit the entire external ear, it has no specific grooves or ridges. Rather, the soft cushioning material assumes the complementary shape of the external ear when under pressure.

As in the embodiments having a complementary contour, this embodiment may also enjoy the advantage of a more comfortable fit and better sound baffling characteristics. Also the usual semicircular fitting means is dispensed with. This contributes to a better overall fit and also allows head gear to be worn. And as shown in FIG. 19, the contour functions as a backing for the latching means, which may be the jointed flexible curved clip, so that when the latching means is applied to the back of the ear lobe, the external ear is pressed against the cushioning material. And the cushioning material may also have a supporting base (442, 443) for further improving the fit and comfort of the device. The supporting base should be attached to the interior of the sound baffling cups and may be a necessity when the cushioning material is a flexible material requiring support.

Another particular of the invention is in combination with a head phone set having speakers (446, 447) attached to a connecting means (448) for connecting said speakers to a playback unit, the improvement comprising;

A fitting means having sound baffling cups (449, 450) for placing said speakers against the ears during operation, said speakers attached to the interior of said sound baffling cups, said fitting means having a sound permeable cushioning material (451, 452) fastened to the interior of said sound baffling cups, so that said cushioning material assumes a shape that is complementary to the shape of the external ear when said external ear is pressed against it, and;

said fitting means further having a latching means (456, 457) for latching onto said sound baffling cups, said latching means pressing and holding the external ear against said cushioning material such that the external ear is substantially sealed against said cushioning material by said latching means, so that the ambient noise reaching the ears during operation is substantially reduced by said sound baffling cups, thereby improving the audibility and perceived rendition of the sound emanating from said speakers.

The latching means may be the jointed flexible curved clip or any one of a number of other embodiments that may latch the sound baffling cups against the ears and seal the ear lobe against the cushioning material or complementary contour as the case may be. And the cushioning material may also have a supporting base (453, 454) for further improving the fit and comfort of the device. The supporting base should be attached to the interior of the sound baffling cups and may be a necessity when the cushioning material is a flexible material requiring support.

Figure 20:
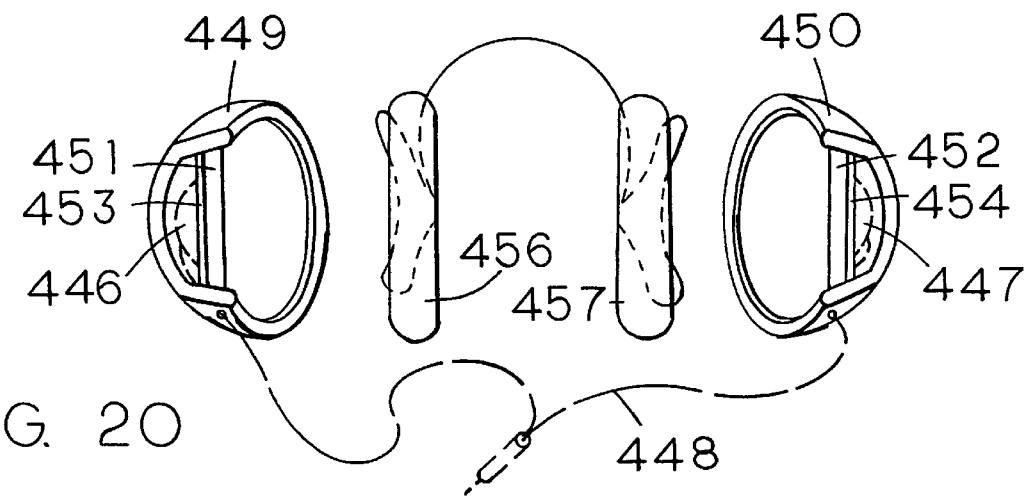
FIG. 20 shows how the latching means and the cushioning material that should be used for head phone sets combines with sound baffling cups and some of the previously known art.

The difference, for embodiments describing the use of sound baffling cups, between those embodiments that have speakers and those embodiments that have none is that the first are head phone sets whereas the second are sets of ear protectors. Accordingly, the embodiments that have speakers may have all the features of the embodiments that do not have speakers, excepting the hole (407, 415, 455, 458) which is used to allow the connecting means to pass from the speakers through the sound baffling cups to the connecting means connection. Although the holes that have been given reference numerals lie in FIG. 18 and FIG. 20, it should be noted that further holes serving the same purpose are to be found in subsequent drawings of sound baffling cups having a semicircular fitting means. And in these embodiments the connecting means will often be comprised of wires although it could also be comprised of fiber optic cable.

For all of the embodiments that have a cushioning material or complementary contour a material that may serve well is foam rubber. When used for a complementary contour, the foam rubber will require more stiffness than necessary for use as a cushioning material. This is needed to preserve the topography of the complementary contour under pressure. Accordingly, for all of these embodiments it may be preferable that the cushioning material or complementary contour is made of foam rubber.

However, to minimize the sound that may travel through gaps between the contour and the external ear during operation, a skin adhering material may be used. It may therefore be preferable that said cushioning material or complementary contour has a binding preference for skin, said binding preference substantially sealing said cushioning material or complementary contour against the external ear, so that the fit and sound baffling characteristics of said device are substantially improved.

As further shown FIGS. 21, 22, 23, and 24, according to another particular the invention is comprised of a jointed flexible curved clip having two parts, the first part (460) shaped to fit the curvature of the anterior half of the lip (462) of said sound baffling cups, the second part (464) shaped to fit the curvature of the posterior half of the lip of said sound baffling cups, and;

the first part of said jointed clip attached by a first hinge (466) to a first pivot (468) mounted in a seat (470) projecting from the inferior part of said sound baffling cups, the second part of said jointed clip attached by a second hinge (472) to a second pivot (474) mounted in the distal end of said first part, and;

the first and second parts of said jointed clip further having a lip groove (476, 477) for accommodating the lip of said sound baffling cups, the distal end of the second part further having a tongue (478) for latching into a tongue groove (480) located on the lateral surface (481) of said seat, such that said jointed clip further provides a firm backing for the external ear when locked in place by said lip groove and by said tongue groove, and;

the lateral surface (482) of said jointed clip having supporting material (483) for sealing said jointed clip against the ear lobe, so that when said jointed clip is pivoted to fit the lip of said sound baffling cups into said lip groove and latch said tongue in said tongue groove during operation, the supporting material of said lateral surface of said jointed clip presses laterally to seal the ear lobe against a surface selected from the group consisting of the complementary contour or the cushioning material, as the case may be, and;

the medial surface (484) of said jointed clip having a wedge shaped layer of bracing material (486) applied to it, the thicker part of said wedge shaped layer attached to the posterior circumference (488) of said second part, the thinner part of said wedge shaped layer comprising a frontal pad (490) for sealing and fitting the anterior part of said device against the head and jawbone, and;

said bracing material further having a lip contour (492) for complementing the shape of the head and neck during operation, such that said lip contour curves the bracing material of said jointed clip laterally away from the head where it touches the jaw bone and the side arch of the skull, and said lip contour curves the bracing material of said jointed clip medianly towards the head and neck where it touches the human body surface beneath the jaw bone and the external ear, so that when said sound baffling cups (494) are locked in place by said jointed clip the posterior of said sound baffling cups is moved laterally by said wedge shaped layer of bracing material, thereby pressing and sealing the frontal pad against the head and jaw bone.

This embodiment is one of several that may be used to hold sound baffling cups against the ears. The clip is comprised essentially of two semicircular arcs that have a width greater than the width of the lips of the sound baffling cups. The width must also be sufficient for wedging the ear lobe upward against the cushioning material or the complementary contour as the case may be. The first part of the clip is attached by a first hinge to a first pivot located in a seat projecting from the inferior part of the sound baffling cups. The second part of the clip is attached by a second hinge to a second pivot attached to the distal end of the first part of the clip. Also the clips are designed to provide a firm backing for the ear lobe and the lips of the sound baffling cups when locked in place. They are aided in this by the lip contour and the wedge shape of the bracing material. The resulting shape braces the assembly against the head and neck and also prevents peripheral sound from penetrating through the ear lobe.

To fit the sound baffling cups against the ears, the clips are rotated away from the sound baffling cups to allow the sound baffling cups to be placed against the ears. The first part of the clip is then rotated to fit around the anterior part of the external ear until the lip of the sound baffling cups catches in the lip groove of the clip. Thereafter, the second part of the clip is rotated to fit behind the ear lobe until the lip of the sound baffling cups catches in the lip groove of the second part of the clip and the tongue latches in the tongue groove. When this operation is completed the clip will be pushing the ear lobe laterally into the complementary contour or the cushioning material as the case may be, thereby effectively sealing the external ear against the sound baffling cups.

The sealing of the ears is further aided by the lip contour applied to the medial surface of the wedge shaped layer of bracing material. The second part of the jointed clip occupies a space dimensioned somewhat like a large orange slice, with the thick part of the slice positioned along the posterior circumference of the sound baffling cups. Hence, when locked in place with the lip contoured bracing material wedged against the head and neck, the jointed clip forces the rear of the sound baffling cups and the ear lobe away from the head and neck. This in turn forces the front of the sound baffling cups inward, thereby increasing the sealing effect.

Alternatively as shown in FIGS. (25, 26, 27, 28, 29), the latching means may be comprised of a sliding clip (500) which is attached to the posterior half of the sound baffling cups (501). Essentially the sliding clip performs the same function as, and has a second arc shaped flange (502) dimensioned somewhat like the second part of the jointed clip. The first part of the jointed clip now appears as a first arc shaped flange (504) fused with the anterior half of the sound baffling cups and occupying substantially the same dimension and position as the first part of the jointed clip occupies during operation.

However, the sliding clip also has a lune shaped shell (506) having a curvature corresponding to the shape of the sound baffling cups to which it is attached. This tune shaped shell fits laterally over the posterior part of the sound baffling cups and is attached to the sound baffling cups by a holding means which may be comprised of two strips or bands of elastic material (512, 514) which are held in place by washers or plates (516, 517, 518, 519) that are cemented or fixed into the walls of the sliding clip or sound baffling cups. As shown in the drawings, the holding means allows the elastic material to be attached to both the lateral surface of the sound baffling cups and to the medial surface (520) of the sliding clip.

In operation the sliding clip is pulled back to allow the sound baffling cups to be placed against the external ear so that the first arc shaped flange is wedged in behind the anterior part of the external ear. Then, in the presence of the elastic tension, the sliding clip is guided forward so that the tune shaped shell is positioned proximally to the lateral surface (508) of the sound baffling cups. Simultaneously the second arc shaped flange, which is a part of the sliding clip, slides forward to fit in behind the posterior part of the external ear and substantially seal the second arc shaped flange against the posterior external ear and against the first arc shaped flange.

To further improve its fit the sliding clip also has a lip groove for accommodating the posterior lip of the sound baffling cups. And when the sliding clip is pushed forward to mate with the sound baffling cups, in the region where the first and second arc shaped flanges overlap, the second arc shaped flange fits laterally over the first arc shaped flange. As well, the first and second arc shaped flange have a supporting material (524, 526) for sealing the sliding clip against the ear lobe attached to their lateral surface. And the medial surfaces (528, 530) of the first and second arc shaped flange may also have a wedge shaped layer of bracing material (532) applied to them, so that the thicker part of the wedge shaped layer is attached to the posterior circumference (534) of the sliding clip and the thinner part of the wedge shaped layer comprises a frontal pad (536) attached to the first arc shaped flange, for sealing and fitting the anterior part of the device against the head and jaw bone. As said before, the wedge shaped layer of bracing material may also have a lip contour (538) for complementing the shape of the head and neck during operation. Hence, the posterior part of the device should be moved laterally by the wedge shape of the bracing material during operation, so that the frontal pad is braced against the head and jaw bone.

As shown in the cross-sectional view of FIG. 30, another particular of the invention is in combination with a head phone set having speakers (550, 552) attached to a fitting means (554) for placing said speakers against the ears and a connecting means (556) for connecting said speakers to a playback unit, the improvement comprising;

A pair of sound baffling cups (558, 560) inserted between said speakers and said fitting means, said speakers attached to the interior of said sound baffling cups, said sound baffling cups fully enclosing the ears between said sound baffling cups and the head and neck during operation, so that the ambient noise reaching the ears during operation is substantially reduced, thereby improving the audibility and perceived rendition of the sound emanating from said speakers.

This embodiment simply defines the combination of previously known sound baffling cups with head phone sets. The advantage of this use lies in the reduction of the ambient noise, thereby improving the audibility and perceived rendition of the sound emanating from the speakers of the head phone set. And, with the playback unit turned off, the head phone set may be simply be used as a sound baffling device for reducing the ambient noise. Also, the use of snugly fitting sound baffling cups increases the comfort and fit of the head phone set to some extent, since previous units using speakers padded with foam rubber were given to slippage and were difficult to keep in exact positioning with regards to the ears. In a further improvement suitable for some applications, the sound baffling cups may often have a sound attenuating material such as foam rubber inserted between the speakers and the opening of the sound baffling cups to improve the audibility and perceived rendition of the rendered sound.

As shown in FIG. 31, another particular of the invention is in combination with a head phone set having speakers (562, 563) attached to a fitting means (564) for placing said speakers against the ears and a connecting means (566) for connecting said speakers to a playback unit, the improvement comprising;

A pair of sound baffling cups (568, 570) for fully enclosing the ears between said sound baffling cups and the head and neck during operation, said sound baffling cups inserted between said speakers and said fitting means, said speakers attached to the interior of said sound baffling cups, so that the ambient noise reaching the ears during operation is substantially reduced, thereby improving the audibility and perceived rendition of the sound emanating from said speakers, and;
   A cushioned lip contour (572, 574) for complimenting the shape of the head and neck during operation, said cushioned lip contour applied to the lips (576, 578) of said sound baffling cups such that said cushioned lip contour curves the lips of said sound baffling cups laterally away from the head where it touches the jaw bone and the side arch of the skull, and said cushioned lip contour curves the lips of said sound baffling cups medianly towards the head and neck where it touches the human body surface beneath the jaw bone and behind the inferior external ear, so that the comfort, fit, and sound baffling qualities of said sound baffling cups are substantially improved by said cushioned lip contour.

As stated when describing the application of a cushioned lip contour to the sound baffling cups of ear protectors, a contoured device provides a better fit and comfort. Also the exclusion and baffling of sound is to some extent dependent on the ability of the sound baffling cups to seal against the head and neck, because this prevents the sound from entering through gaps where the lips of the sound baffling cups are joined against the head and neck. A lip contour aids in achieving a proper seal, especially under conditions of stress, where the head and neck are bent or when the sound baffling cups are jarred by external contact.

If we consider the lips of previously available sound baffling cups to lie in a sagittal plane parallel to the side of the head during operation, then as shown in FIG. 15, the lip contour (360, 362) diverges from this plane by curving laterally (368) away from the head and neck directly above the jaw bone (372). Beneath the jaw bone and the inferior external ear (374) the contour diverges from this plane by curving medianly (370) towards the head and neck. This compensates for the hollow (375) of the human body surface found just beneath where the head and neck and jaw bone join. Then, behind the posterior external ear, the contour moves back towards and into this sagittal plane, lying substantially in this plane above the external ear.

As shown in FIG. 32, in another particular of the invention a first part of the connecting means (581, 582) which connects to the far speaker (580) is carried along said fitting means (583) and gathered together to form a bundle (584) with a second part (585, 586) of the connecting means which connects to the near speaker (587), both the first and second part of said connecting means extending from said bundle to connect with the connecting means connection (588), so that when said connecting means connection is connected to the playback unit connector, a single path is followed by said connecting means from the speakers of said head phone set to said playback unit.

Since most previous devices used two speakers, the general procedure has been to run the connecting means from each speaker into a common node, thereby forming a Y shaped arrangement. However, this arrangement tends to encumber the head and neck. often causing the connecting means to become tangled in jackets, hair etc. By gathering the connecting means from one speaker and passing it along the fitting means to the other speaker, the Y shaped connecting means is avoided, thereby allowing the connecting means to follow a single path. This arrangement may be more convenient as it is less likely to interfere with other activities.

Rather than carrying the first part of the connecting means along the fitting means by means of a wiring arrangement, it may be preferable to use the fitting means as an insulating substrate for conductive strips (589, 590, 591, 592) which carry the first part of the connecting means along the fitting means. In FIG. 27, the conductive strips (589, 591) running along the top of the fitting means are electronically connected by contacts (593, 594) which are attached to the restraining bands of the fitting means. The conductive strips (590, 592) running along the side of the fitting means are in continuous contact with each other. These factors ensure that the fitting means may function reliably as a substrate for the conductive strips of the connecting means.

Because this type of connecting means is lopsided, running along one side of the head and neck only, it has a tendency to tug at the sound baffling cups from the side on which it is located. It is therefore preferable that a first section (595) of the connecting means which extends from said bundle to the connecting means connection (596) is formed in the shape of a helix, the shape of said helix maintained by elastic tension, such that said first section is able to expand and contract by means of said elastic tension in response to stresses created by the movements of the head and neck, thereby preventing the sound baffling cups from tugging at the head and neck when said stresses are manifest. As shown in FIG. 33, the helical shape effectively functions as a spring, taking up the slack of the connecting means when necessary, and allowing the connecting means to expand under tension when the head and neck is turned to an unusual degree.

Figure 34:
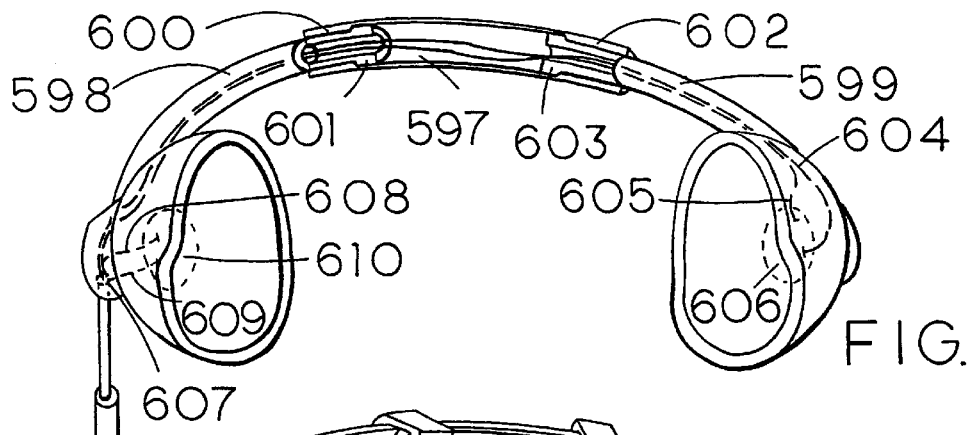
FIG. 34 shows how the single path connecting means may be passed through the tubular tunnel within a hollow tubular fitting means.

Furthermore, as shown in FIG. 34, by using a fitting means comprised of hollow tubular segments, it is possible to pass the connecting means from one speaker to the other through the hollow tubular segments of the fitting means. As illustrated, the middle tube (597) functions as a guide for the first tube (598) and the second tube (599). This eliminates unsightly wiring arrangement and also creates greater compactness of engineering. It is therefore preferable that said fitting means is comprised of elastic hollow tubular segments (597, 598, 599) fashioned to allow a smaller tubular segment (598, 599) to slide fixedly within a larger tubular segment (597), said hollow tubular segments having a restraining means (600, 601, 602, 603) to prevent separation, and;

wherein the length of the arc described by said fitting means is set by sliding said smaller tubular segment to a preferred position within said larger tubular segment, so that the length of the arc may be reduced sufficiently to allow said elastic arc shaped tubes to be worn behind the neck, and;

the first part (604, 605) of the connecting means which connects to the far speaker (606) is carried through said tubes and gathered together to form a bundle (607) with the second part (608, 609) of the connecting means which connects to the near speaker (610), thereby improving the appearance, comfort and utility of said device. This embodiment may also be fashioned from a larger elastic arc shaped tube and a smaller elastic arc shaped tube. And the retraining means of this embodiment is formed by means of the interlocking tube ends (600, 601) and (602, 603). The tight frictional fit of the tubes allows the size of the arc to be adjusted by the frictional feed.

Because the lips of the sound baffling cups form a more stable foundation than the loosely fitting padded speakers or plug-in speakers of some previous head phone sets, it is possible to apply more elastic tension to head phone sets using sound baffling cups. When the elastic tension is increased by a suitable amount, the arc shaped fitting means used in some previous devices may be worn in an arc behind the neck. It is therefore preferable that said fitting means is comprised of two slidably connected elastic arc shaped bands to which the sound baffling cups are attached, and;

wherein the improvement comprises an increase in the tension applied by said arc shaped band to the sound baffling cups, so that when said arc shaped bands are shortened so as to be worn behind the neck, said increase in the tension allows said sound baffling cups to maintain a snug fit against the ears, thereby improving the comfort and utility of said device.

Figure 35:
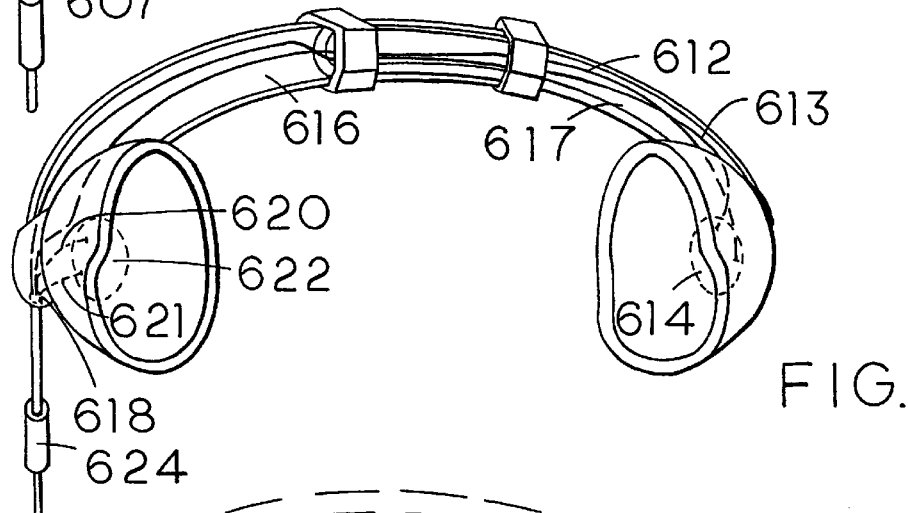
FIG. 35 shows how the single path connecting means may be carried within the grooves of a fitting means comprised of arc shaped bands.

The advantage of placing the fitting means in this fashion is that it is less obtrusive and that head gear may be worn. This embodiment may be improved further by providing arc shaped bands that are grooved. The tubular grooves serve as a guide for the connecting means and allow it to be passed more easily from the far speaker to the near speaker. Therefore as shown in FIG. 35, according to another particular of the invention it is preferable that said elastic arc shaped bands are grooved, and;

a first part (612, 613) of the connecting means which connects to the far speaker (614) is carried through said elastic arc shaped bands (616, 617) and gathered together to form a bundle (618) with a second part (620, 621) of the connecting means which connects to the near speaker (622), both the first and second parts of said connecting means extending from said bundle to connect with the connecting means connection (624), so that when said connecting means connection is connected to the playback unit connector, a single path is followed by said connecting means from the speakers of said head phone set to said playback unit, thereby improving the appearance, comfort and utility of said device.

Figure 36:
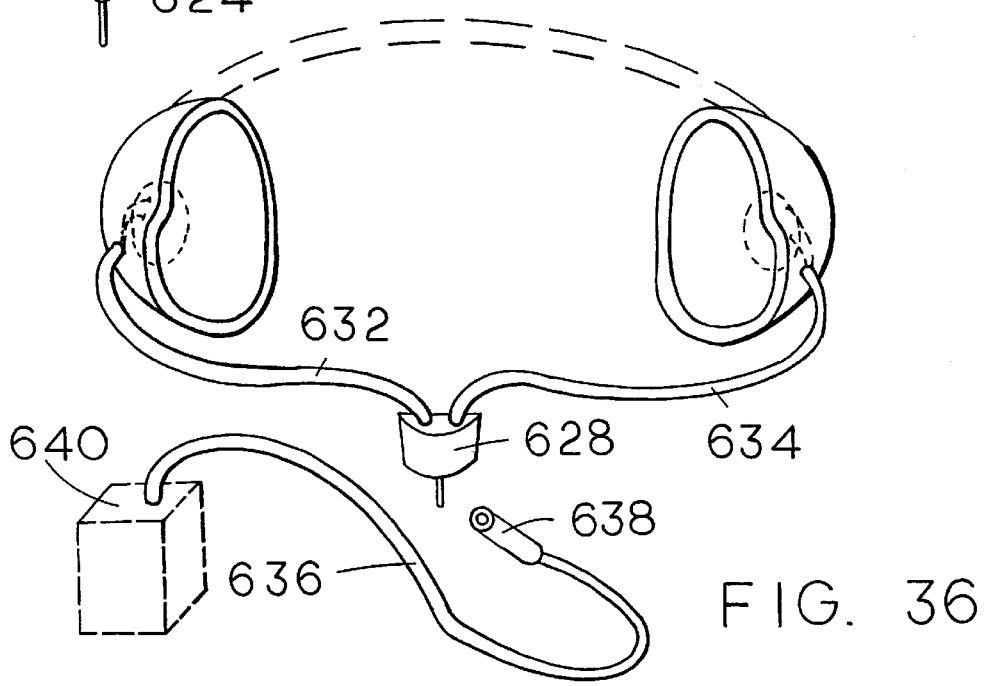
FIG. 36 shows how the Y-shaped arrangement of previous devices can be improved by moving the connecting means connection to the fork of the Y.

As shown in FIG. 36, according to another particular of the invention it is preferable that said connecting means is the Y shaped arrangement shown by some previous devices and wherein the improvement comprises the placement of the connecting means connection (628) at the fork of said Y-shaped arrangement, such that the fork of said Y-shaped arrangement is formed by attaching the first part (632) and second part (634) of said connecting means to said connecting means connection, and;

wherein the improvement further comprises a playback unit extension (636) of sufficient length to extend from said playback unit to said connecting means connection, the end of said playback unit extension having the playback unit connector (638) to which said connecting means connection corresponds, so that the playback unit (640) may be connected to said improved head phone set by connecting said connecting means connection to said playback unit connector.

Another problem which some previous devices experienced was the degrading of the connecting means. This was caused largely by the tendency of the connecting means to snag while the device was being used. The stresses to which these snags subjected the connecting means were aggravated by the tendency of the connecting means connection to bind in the playback unit plug-in connector.

This embodiment may remedy these deficiencies by moving the connecting means connection to the fork of the Y, where the same bind will not occur. The two parts of the connecting means that comprise the branches of the Y are then permanently connected directly to the connecting means connection which then connects these branches to form the fork of the Y. And the playback unit plug-in connector (We use plug-in here as the previous art usually used female connectors in wiring arrangements. However the connectors could also be male, especially when used in a playback unit extension. Hence plug-in denotes either male or female.) is extended from the playback unit to meet the connecting means connection at the fork of the Y. This allows the connecting means connection to be easily pulled from the playback unit plug-in connector when the connecting means is snagged, thereby minimizing the stress to which the connecting means is subjected.

It is possible to fashion the construction of the playback unit extension so that it is automatically retractable. This may be done by providing a spring loaded uptake spool for the extension. It may therefore be preferable that said playback unit extension retracts automatically into said playback unit when disconnected from said connecting means connection.

The tension provided by the retracting means must be slight, just enough to wind the playback unit extension back onto the uptake spool upon disconnection from the connecting means connection. In operation, the latching of the connecting means connection in the playback unit plug-in connector should be sufficient to keep the playback unit extension from pulling free and rewinding.

The connecting means may be the usual wiring arrangement shown in many previous devices. But it may also be comprised of fibre optic cable or it could be fashioned from wire-less or infra red radiation devices. The fibre optic cable confers a better quality to the connecting means, whereas the wire-less or infra red radiation eliminate the wiring arrangement thereby making the connecting means less obtrusive.

Figure 37:
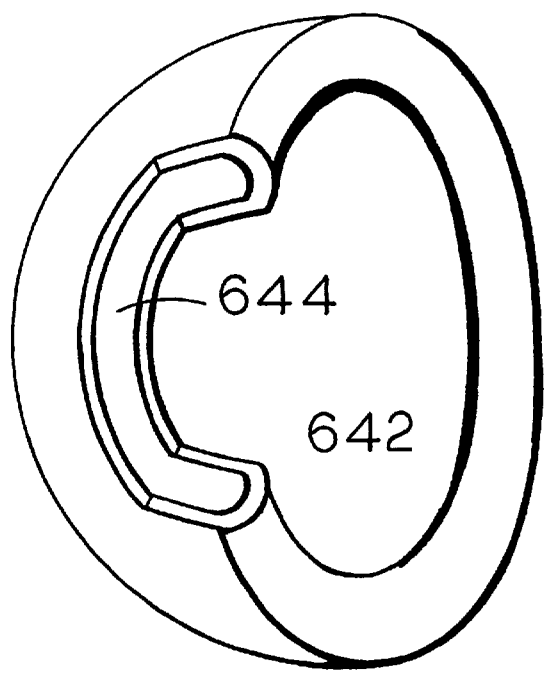
FIG. 37 shows how an enclosure containing a vacuum may be used to improve the sound baffling cups of head phone sets and ear protectors. This figure does not appear in order, but rather may be found right after FIG. 12 in the drawings. This minimizes the number of sheets.

As shown in FIG. 37, according to another particular of the invention it is preferable that the material forming said sound baffling cups (642) has a cup shaped enclosure (644) containing a vacuum, said enclosure extending substantially throughout the entire body of said sound baffling cups, so that the ambient noise reaching the ears during operation is substantially reduced by said enclosure, thereby improving the audibility and perceived rendition of the sound emanating from said speakers.

As discussed in the summary, a vacuum should be opaque to sound. The inclusion of a vacuum within an enclosure extending substantially throughout the entire body of the sound baffling cups should therefore render the sound baffling cups essentially opaque to sound. Nevertheless, peripheral transmission of sound may still occur along the material of the enclosure. This should however be minimized by an appropriate choice for this material. The inclusion of a vacuum within the sound baffling cups should then improve the sound baffling of these sound baffling cups and thereby reduce the ambient noise or improve the audibility and perceived rendition of the sound emanating from the speakers.

What is claimed is:

1. A sound baffling device comprised of at least one enclosure containing a homogeneous means for attenuating sound, said sound baffling device further comprising a means for admitting and removing matter having a connection to said enclosures, said connection fashioned to enable the admitting and removing of matter to and from said enclosures, so that the sound baffling characteristics of said sound baffling device can be varied by said admitting and removing of matter, and;

said sound baffling device further comprising
a means for measuring the values and characteristics of the ambient sound, and
a means for correlating having default parametric values and characteristics, and;
said means for correlating using the correlation between said measured values and characteristics of the ambient sound and said default parametric values and characteristics as a benchmark for adjusting said means for admitting and removing of matter, so that matter is admitted and removed from said enclosures as indicated by said benchmark, and;
the measured values and characteristics of the ambient sound throughout the physical space which is governed by said sound baffling device enter a convergence towards said default parametric values and characteristics,
so that after a requisite interval of time an optimum correlation between said default parametric values and characteristics and said measured values and characteristics of the ambient sound is attained.

2. The sound baffling device of claim 1 further comprising an input means for entering and storing input parametric values and characteristics,
said input means, said means for measuring, and said means for correlating in combination comprising a controlling means, and;
said controlling means ensuring that any of said input parametric values and characteristics stored through said input means are used to replace the corresponding default parametric values and characteristics of said means for correlating in operation,
so that said means for correlating uses the correlation between said measured values and characteristics of the ambient sound and the parametric values and characteristics to create said benchmark defined in claim 1, and matter is admitted and removed from said enclosures as indicated by said benchmark,
so that the measured values and characteristics of the ambient sound throughout the physical space which is governed by said sound baffling device enter a convergence towards said parametric values and characteristics,
whereby after a requisite interval of time an optimum correlation between said parametric values and characteristics and said measured values and characteristics of the ambient sound is attained.

3. The sound baffling device of claim 2 further comprising a microprocessor governed by a controlling program, said controlling program having an acoustic model of the physical space governed by said sound baffling device, said acoustic model devised to operate in accordance with the principles of acoustic science, and;
said controlling program capable of calculating predicted values and characteristics of the ambient sound which should result from certain dispositions of matter within said enclosure, and;
said controlling program further using the correlation between said predicted values and characteristics and the parametric values and characteristics to create a further benchmark, and;
said controlling program using said further benchmark and said benchmark of claim 2 to calculate instructions for said means for correlating, and;
said means for correlating using said instructions to adjust said means for admitting and removing of matter, so that matter is admitted and removed from said enclosures as indicated by said instructions, and;
the measured values and characteristics of the ambient sound throughout the physical space which is governed by said sound baffling device enter a convergence towards said parametric values and characteristics, and;
after a requisite interval of time an optimum correlation between said parametric values and characteristics and said measured values and characteristics of the ambient sound is attained.

4. In combination with two sound baffling cups for enclosing the external ears during operation, the improvement comprising;
a cup shaped enclosure containing air or a rarefied gas or a rarefied mixture of gases, such that the state of rarefaction of said rarefied gas or said rarefied mixture of gases is a state of rarefaction consisting of a range varying from a lesser pressure of 10 Pascals to a greater pressure of 70,000 Pascals, so that a preferred amount of sound is transmitted through said enclosure, said enclosure extending substantially throughout the entire body of said sound baffling cups, so that the ambient noise reaching the ears during operation is substantially reduced by the state of rarefaction contained within said enclosure, and;
a fitting means for placing said sound baffling cups against the ears, said fitting means having a cushion fastened to the interior of said sound baffling cups, and;
said fitting means further having a latching means for pressing and holding the external ear against said cushion such that the external ear is substantially sealed against said cushion by said latching means, said latching means comprised of a sliding clip or a jointed clip, and;
wherein said sliding clip is comprised of a lune shaped shell having a curvature corresponding to the shape of the posterior portion of said sound baffling cup, said sliding clip further having a lip groove for accommodating a posterior portion of the lip of said sound baffling cup, said lip groove embedded in a second arc shaped flange attached to the medial end of said sliding clip, so that when said sound baffling cup is attached to the ear by wedging the first arc shaped flange, that is attached to the anterior arc of the lip of said sound baffling cup, in behind the anterior portion of the external ear, said second arc shaped flange may be movably fitted behind the posterior portion of the external ear, so that in operation said second arc shaped flange is fitted laterally over said first arc shaped flange and the lune shaped shell is positioned proximally to the lateral surface of said sound baffling cup, whereby the external ear is grasped between said arc shape flanges and said sound baffling cup so that said sound baffling cup is attached to the ears by said sliding clip, or;

wherein said jointed clip has two parts, the first part shaped to fit the curvature of the anterior half of the lip of said sound baffling cups, the second part shaped to fit the curvature of the posterior half of the lip of said sound baffling cups, and;

the first part of said jointed clip attached by a first hinge to a first pivot mounted in a seat projecting from the inferior part of said sound baffling cups, the second part of said jointed clip attached by a second hinge to a second pivot mounted in the distal end of said first part, and;

the first and second parts of said jointed clip further having a lip groove for accommodating the lip of said sound baffling cups, the distal end of the second part further having a tongue for latching into a tongue groove located on the lateral surface of said seat, such that said jointed clip further provides a firm backing for the external ear when locked in place by said lip groove and by said tongue groove, and;

the lateral surface of said clips having a supporting material for sealing said clips against the ear lobe, so that when said clips are latched against the ear during operation, the supporting material of said lateral surface of said clips presses laterally to seal the ear lobe against said cushion, and;

the medial surface of said clips having a wedge shaped layer of bracing material applied to it, the thicker part of said wedge shaped layer attached to the posterior circumference of said second arc shaped flange or said second part, the thinner part of said wedge shaped layer comprising a frontal pad for sealing and fitting the anterior part of said clips against the head and jawbone, and;

said bracing material further having a cushioned lip contour for complementing the shape of the head and neck during operation, such that said cushioned lip contour curves the bracing material of said clips laterally away from the head where it touches the jaw bone and the side arch of the skull, and said cushioned lip contour curves the bracing material of said clips medially towards the head and neck where it touches the human body surface beneath the jaw bone and the external ear, so that when said sound baffling cups are locked in place by said clips the posterior of said sound baffling cups is moved laterally by said wedge shaped layer of bracing material, thereby pressing and sealing the frontal pad against the head and jawbone, so that the ambient noise reaching the ears during operation is substantially reduced by said sound baffling cups.

5. The device of claim 4, wherein said cushion is a complementary contour, so that said complementary contour corresponds substantially to the convolutions of the external ear by means of a plurality of flexible cushioning grooves and ridges.

6. The improved device of claim 4 or claim 5, wherein said cushion is a sound permeable cushion, and;

further comprising a pair of speakers, each speaker of said pair of speakers attached to the interior of one of said sound baffling cups, said pair of speakers electronically connected to a connecting means having a connecting means connection for making electronic connection to a playback unit, so that the ambient noise reaching the ears during operation is substantially reduced, thereby improving the audibility and perceived rendition of the sound emanating from said pair of speakers.

7. A controlling means, said controlling means having an input means for entering and storing parametric values and characteristics, and;

said controlling means further having a means for measuring the values and characteristics of the ambient sound throughout the physical space governed by said controlling means, said means for measuring having sensor inputs, and;

said controlling means further having a means for correlating the measured values and characteristics to the parametric values and characteristics, and;

said means for correlating using the correlation between said measured values and characteristics and said parametric values and characteristics as a benchmark for adjusting the elements of the physical space to improve said correlation, so that the measured values and characteristics throughout the physical space which is governed by said controlling means enter a convergence towards said parametric values and characteristics, and;

said controlling means further comprising a microprocessor governed by a controlling program, said controlling program having an model of the physical space governed by said controlling means, said model devised to operate in accordance with the principles of acoustic science, and;

said controlling program capable of calculating predicted values and characteristics of the ambient sound which should result from certain dispositions of said elements, and;

said controlling program further using the correlation between said predicted values and characteristics and the parametric values and characteristics to create a further benchmark, and;

said controlling program using said further benchmark and said benchmark to calculate instructions for said means for correlating, and;

said means for correlating using said instructions to adjust said elements of the physical space, so that said measured values and characteristics of the ambient sound throughout the physical space that is governed by said controlling means enter a convergence towards said parametric values and characteristics, whereby after a requisite interval of time an optimum correlation between said parametric values and characteristics and said measured values and characteristics is attained.

8. The sound baffling device of claim 1 or claim 3 or claim 2 characterized by the splitting of the sound energy into a reflected and a transmitted component, so that the distribution of said reflected and transmitted component is determined by the shape of the enclosure in combination with the degree of rarefaction therein, and;

wherein said shape of the enclosure is selected from at least one of a sphere, a hemisphere, a zone and segment of one base, a zone and segment of two bases, a spherical sector, a lune, a cylinder, a cone, an elliptic paraboloid, a hyperboloid of one sheet, a hyperbolic paraboloid, an ellipsoid, a torus, a pyramid, a moebius strip, a klein bottle, a handle, a concave polyhedron, or a convex polyhedron.

9. The sound baffling device of claim 1 or claim 2 characterized by the splitting of the sound energy into a reflected and a transmitted component, so that the distribution of said reflected and transmitted component is determined by the shape of the enclosure in combination with the degree of rarefaction therein, and;

wherein the enclosure is shaped like a hollow sheet extending in both the x direction and the z direction of the xz plane, the upper and lower surfaces of said sheet having a curvature given by their divergence from the xz plane, so that said curvature is definable as a function of the y co-ordinate of the xyz co-ordinate system.

10. The sound baffling device of claim 1 or claim 3 or claim 2 characterized by the splitting of the sound energy into a reflected and a transmitted component, so that the distribution of said reflected and transmitted component is determined by the shape of the enclosure in combination with the degree of rarefaction therein, and;

wherein the enclosure is shaped like a hollow sheet extending in both the x direction and the z direction of the xz plane, the upper and lower surfaces of said sheet being substantially equidistant from each other and having a curvature given by a mathematical relationship defined in the xy plane, said relationship selected from at least one of a sinusoid curve, a sine curve, an inverse sine curve, a hyperbolic sine curve, a cosine curve, an inverse cosine curve, a hyperbolic cosine curve, a tangent curve, an inverse tangent curve, a hyperbolic tangent curve, a secant curve, an inverse secant curve, a hyperbolic secant curve, a cosecant curve, an inverse cosecant curve, a hyperbolic cosecant curve, a cotangent curve, an inverse cotangent curve, a hyperbolic cotangent curve, a logarithmic curve, a parabola, a semicubical parabola, a cubical parabola, a trajectory curve, a hyperbola, a rectangular hyperbola, an equilateral hyperbola, an ellipse, a circle, an evolute of an ellipse, an involute of a circle, an equiangular spiral, a hyperbolic spiral, a parabolic spiral, a spiral of Archimedes, a companion to the cycloid, a cycloid, a witch of agnesi, a hypocycloid, a deltoid, an astroid, a nephroid, an epicycloid, a cochleoid, a stropheoid, a conchoid of Nicomedes, a folium of Descartes, a bifoleum, a lemniscate of Bernouilli, an n-leaved rose, an oval of Cassini, a limacon of Pascal, a cardioid, a cissoid of Diocles, a serpentine curve, a lituus, a tractrix, a power function curve, an exponential curve, a probability curve, a gamma function curve, a quadratic of Hipplas.

11. The sound baffling device of claim 10 characterized by the splitting of the sound energy into a reflected and a transmitted component, such that the distribution of said reflected and transmitted component is determined by the shape of the enclosure in combination with the degree of rarefaction therein, and;

wherein the enclosure has a further curvature given by a mathematical relationship defined in the yz plane, said relationship selected from at least one of a sinusoid curve, a sine curve, an inverse sine curve, a hyperbolic sine curve, a cosine curve, an inverse cosine curve, a hyperbolic cosine curve, a tangent curve, an inverse tangent curve, a hyperbolic tangent curve, a secant curve, an inverse secant curve, a hyperbolic secant curve, a cosecant curve, an inverse cosecant curve, a hyperbolic cosecant curve, a cotangent curve, an inverse cotangent curve, a hyperbolic cotangent curve, a logarithmic curve, a parabola, a semicubical parabola, a cubical parabola, a trajectory curve, a hyperbola, a rectangular hyperbola, an equilateral hyperbola, an ellipse, a circle, an evolute of an ellipse, an involute of a circle, an equiangular spiral, a hyperbolic spiral, a parabolic spiral, a spiral of Archimedes, a companion to the cycloid, a cycloid, a witch of agnesi, a hypocycloid, a deltoid, an astroid, a nephroid, an epicycloid, a cochleoid, a stropheoid, a conchoid of Nicomedes, a folium of Descartes, a bifoleum, a lemniscate of Bernouilli, an n-leaved rose, an oval of Cassini, a limacon of Pascal, a cardioid, a cissoid of Diocles, a serpentine curve, a lituus, a tractrix, a power function curve, an exponential curve, a probability curve, a gamma function curve, a quadratic of Hippias, and;

said curvature combined with the curvature defined in claim 10 by taking the y co-ordinate of said mathematical relationship defined in the xy-plane and combining it with the y co-ordinate of said mathematical relationship defined in the yz-plane, so that the resulting y co-ordinates are the y co-ordinates of the curvature of said enclosure in the xyz co-ordinate system.

12. The sound baffling device of claim 1 or claim 3 or claim 2 further comprising a large vacuum chamber connected by a pipe having a chamber valve to said sound baffling device, said vacuum chamber maintained in a state of vacuum by said means for admitting and removing, so that when said controlling means of claim 1 causes said chamber valve to open, matter present within said enclosures, and residing at a pressure higher than the pressure present within said vacuum chamber, flows rapidly into said vacuum chamber, whereby the speed at which said matter is removed from within said enclosures is increased.

13. The sound baffling device of claim 12 wherein said means for admitting and removing is sealed to prevent the entry and exit of matter, and further comprising;

a storage chamber having the capacity for substantially storing all the matter that is present within the enclosures, the piping network, the vacuum chamber, and the vacuum pump, so that the matter present within said means for admitting and removing may be admitted to, or removed from said storage chamber as required by the operation of said means for admitting and removing.

14. The sound baffling device of claim 12 wherein said means for admitting and removing further has a two way valve, said two way valve allowing the admission of matter to said means for admitting and removing, or the venting of matter from said means for admitting and removing.

15. The sound baffling device of claim 13 wherein said matter is a liquid, air, or a gas, or a mixture of gases, or plasma.

16. The device of claim 1 or claim 3 or claim 2 further having improved heat insulating properties, wherein the improvement comprises;

a reflective coating applied to the inner surface of said enclosures, so that the heat insulating characteristics of said enclosures are substantially improved.

17. The sound baffling device of claim 1 or claim 2 having a plurality of supporting struts for counteracting external pressure present at the surface of said enclosure, said supporting struts placed and attached between the walls of said enclosure, so that the structural integrity of said enclosure is maintained.

18. The sound baffling device of claim 1 or claim 3 or claim 2 wherein said means for measuring has sensor inputs placed throughout the extent of the physical space that is governed by said sound baffling device.

19. The sound baffling cups of claim 4 further comprising a means for admitting and removing matter having a connection to said enclosure, said connection fashioned to enable the admitting and removing of matter to and from said enclosure, so that the transmission of sound through said sound baffling cups is increased by said admitting and decreased by said removing of matter.

20. The sound baffling device of claim 4 wherein the step in the process of manufacture which creates said enclosure is carried out within a vacuum chamber containing air or a rarefied gas or a rarefied mixture of gases, such that the state of rarefaction of said rarefied gas or said rarefied mixture of gases is a state of rarefaction consisting of a range varying from a lesser pressure of 10 Pascals to a greater pressure of 70,000 Pascals, so that said state of rarefaction is incorporated into the cavity of said enclosure.

21. The improved head phone set of claim 6, wherein said connecting means is the Y shaped arrangement shown by some previous devices and wherein the improvement comprises the placement of the connecting means connection at the fork of said Y-shaped arrangement, such that the fork of said Y-shaped arrangement is formed by attaching the first and second parts of said connecting means to said connecting means connection, and;

wherein the improvement further comprises a playback unit extension of sufficient length to extend from said playback unit to said connecting means connection, the end of said playback unit extension having the playback unit connector to which said connecting means connection corresponds, so that the playback unit may be connected to said improved head phone set by connecting said connecting means connection to said playback unit connector.

22. The device of claim 21 wherein a first section of the connecting means which extends from said speakers to the connecting means connection is formed in the shape of a helix, the shape of said helix maintained by elastic tension, so that said first section is able to expand and contract by means of said elastic tension in response to stresses created by the movements of the head and neck, thereby preventing the sound baffling cups from tugging at the head and neck when said stresses are manifest.

23. The device of claim 21 wherein said playback unit extension retracts automatically into said playback unit when disconnected from said connecting means connection.

24. The sound baffling device of claim 9, wherein the use of said sound baffling device is selected from the group consisting of the use of said sound baffling device to create walls and ceilings having improved sound attenuation, or the use of said sound baffling device to create bricks or building blocks having improved sound attenuation, or the use of said sound baffling device for the sound proofing of holes and gaps within structures or buildings, or the use of said sound baffling device to create casings having improved sound attenuation for motors, machinery and industrial equipment, or the use of said sound baffling device to create structural components having improved sound attenuation, or the use of said sound baffling device to create movable dividers and partitions that have improved sound attenuation, or the use of said sound baffling device in the sound proofing of automobile, airplane and other vehicular bodies, or the use of said sound baffling device to govern the acoustics of amphitheaters, theaters, lecture halls, classrooms, halls, and corridors, or the use of said sound baffling device in the head phone sets of sound monitoring, communication or entertainment equipment, or the use of said sound baffling device to create directional speakers.

\* \* \* \* \*